(12) United States Patent
Papadakis

(10) Patent No.: US 12,188,056 B2
(45) Date of Patent: Jan. 7, 2025

(54) SIALYLTRANSFERASES FOR IN VIVO SYNTHESIS OF 3'SL

(71) Applicant: DSM IP Assets B.V., Heerlan (NL)

(72) Inventor: Manos Papadakis, Hørsholm (DK)

(73) Assignee: DSM IP Assets B.V., Heerlan (NL)

( * ) Notice: Subject to any disclaimer, the term of this patent is extended or adjusted under 35 U.S.C. 154(b) by 0 days.

(21) Appl. No.: 18/177,070

(22) Filed: Mar. 1, 2023

(65) Prior Publication Data
US 2024/0141307 A1 May 2, 2024

(30) Foreign Application Priority Data
Mar. 2, 2022 (DK) .............................. PA202270077

(51) Int. Cl.
| | | |
|---|---|---|
| *C12N 9/10* | (2006.01) | |
| *C07K 14/24* | (2006.01) | |
| *C12P 19/04* | (2006.01) | |
| *C12P 19/18* | (2006.01) | |

(52) U.S. Cl.
CPC ............ *C12N 9/1081* (2013.01); *C07K 14/24* (2013.01); *C12P 19/04* (2013.01); *C12P 19/18* (2013.01); *C12Y 204/99004* (2013.01)

(58) Field of Classification Search
CPC .... C12N 9/1081; C12N 9/1048; C12N 15/70; C12N 9/1051; C12N 1/16; C12N 1/20; C07K 14/24; C07K 14/195; C12P 19/04; C12P 19/18; C12P 19/26; C12Y 204/99004; C12Y 204/01056; C12R 2001/19
See application file for complete search history.

(56) References Cited

U.S. PATENT DOCUMENTS

| | | |
|---|---|---|
| 2007/0020736 A1 | 1/2007 | Samain |
| 2020/0080095 A1 | 3/2020 | Seo et al. |
| 2020/0140894 A1 | 5/2020 | Liu et al. |
| 2021/0087599 A1 | 3/2021 | Jennewein et al. |

FOREIGN PATENT DOCUMENTS

| | | |
|---|---|---|
| CN | 111133112 | 5/2020 |
| EP | 3575404 A1 | 12/2019 |
| EP | 3789495 A1 | 3/2021 |
| WO | 2007101862 | 9/2007 |
| WO | 2015197082 | 12/2015 |
| WO | 2017152918 | 9/2017 |
| WO | 2017182965 | 10/2017 |
| WO | 2019020707 A1 | 1/2019 |
| WO | WO 2019020707 | 1/2019 |
| WO | WO 2019123324 | 6/2019 |
| WO | 2021123113 | 6/2021 |
| WO | 2021148620 A1 | 7/2021 |
| WO | 2021202883 A1 | 10/2021 |
| WO | WO 2021202883 | 10/2021 |

OTHER PUBLICATIONS

Genbank, "alpha-2,3-sialyltransferase [Pasteurella oralis]", Accession No. WP_101774487.1, Dec. 22, 2023.
Bych et al. 2019, Current Opinion in Biotechnology 56:130-137.
Chen Adv. Carbohydr. Chem. Biochem. 72, 113-190 (2015).
H. H. Freeze and A. D. Elbein: Chapter 4: Glycosylation precursors, in: Essentials of Glycobiology, 2nd edition (Eds. A. Varki et al.), Cold Spring Harbour Laboratory Press (2009)).
Herring and Blattner 2004 J. Bacteriol. 186: 2673-81.
Murphy, J Bacteriol. (1998);180(8):2063-7.
Muyrers et al., EMBO Rep. (2000) 1(3): 239-243.
Needleman and Wunsch, 1970, J. Mol. Biol. 48: 443-453.
Schelch et al 2020, Biotechnology Advances 44, 107613.
Vetcher et al., Appl Environ Microbiol. (2005);71(4):1829-35.
Waddell C.S. and Craig N.L., Genes Dev. Feb. 1988; 2(2):137-49.
Warming et al 2005 Nucleic Acids Res. 33(4): e36.
Wenzel et al., Chem Biol. (2005), 12(3):349-56.
Zhang et al., Nature Genetics (1998) 20: 123-128.
PA202270077, First Technical Examination / Search Report, dated Aug. 30, 2022.
PA202270077, Response to First Technical Examination / Search Report, dated Nov. 21, 2022.
PA202270077, Second Technical Examination, dated Jan. 19, 2023.
PA202270077, Response to Second Technical Examination, dated Feb. 3, 2023.

*Primary Examiner* — Satyendra K Singh
(74) *Attorney, Agent, or Firm* — Neal, Gerber & Eisenberg LLP

(57) ABSTRACT

The present disclosure relates to the production of sialylated Human Milk Oligosaccharides (HMOs), in particular to the biosynthetic production of 3'-sialyllactose (3'SL), and to genetically engineered cells and methods suitable for said production.

20 Claims, 2 Drawing Sheets
Specification includes a Sequence Listing.

SEQUENCE LISTING

```
Sequence total quantity: 54
SEQ ID NO: 1            moltype = AA  length = 301
FEATURE                 Location/Qualifiers
source                  1..301
                        mol_type = protein
                        organism = Campylobacter lari
SEQUENCE: 1
MVGGGNAVIC GNGPSLKNID YKRLPKEFDV FKCNQFYFED RYFVGKNIKY AFFNPFVFFE   60
QYYTSKKLIQ NGEYIIENIV CSTFNLPLID NENFIKLFPS YFCDALLGHE VLAKINDFFA  120
FVKYNEIYEN KRITSGIYMC AAAVALGYKN IYLTGIDFYD DKNNMYAFES KQHNILSLLP  180
NFKNKDSVYE AHSKNFDLET LIFLKEKYNV NFYALNENSP ISKYIDLAPI ENSNFILKDK  240
PSNYINDILI PNSKYKNTIY KVQNQDSKLK QNIYYKLFKD LFHLPSDIKH YLKEKYANKN  300
R                                                                 301

SEQ ID NO: 2            moltype = AA  length = 360
FEATURE                 Location/Qualifiers
source                  1..360
                        mol_type = protein
                        organism = Neisseria gonorrhoeae
SEQUENCE: 2
MIFYTFDRVN QGERNAVSLL KDLFNEEGK  PVNLIFCYTI LQMKVAERIM AQHPGERFYV   60
VLMSENRNEK YDYYFNQIKD KAERAYFFYL PYGLNKSFNF IPTMAELKVK SMLLPKVKRI  120
YLASLEKVSI AAFLSTYPDA EIKTFDDGTN NLIRESSYLG GEFAVNGAIK RNFARMMVGD  180
WSIAKTRNAS DEHYTIFKGL KNIMDDGRRK MTYLPLFDAS ELKAGDETGG TVRILLGSPD  240
```

```
KEMKEISEKA AKNFNIQYVA PHPRQTYGLS GVTALNSPYV IEDYILREIK KNPHTRYEIY   300
TFFSGAALTM KDFPNVHVYA LKPASLPEDY WLKPVYALFR QADIPILAFD DKNQSHGKSK   360

SEQ ID NO: 3            moltype = AA   length = 303
FEATURE                 Location/Qualifiers
source                  1..303
                        mol_type = protein
                        organism = Pasteurella oralis
SEQUENCE: 3
MDEVERSREC KSVVVAGNGA SLTQVDYSLL PVNYDVFRCN QFYFEDHYFL GKKIKAAFFT    60
PGVLLEQYYT LYHLRKNNEY SVDKIILSSF NHPTVDLSKS ENIKKLFIDV INGYEEYLSK   120
LSDFDIYLRY KELYESQRIT SGIYMCAVAI AMGYTDIYLT GIDFYESNSK SYAFEPKKTN   180
IISLLPDFKN ISSKPHYHNK DADLEALYFL QKNYSVNFYS ISPGSLLYEH FPTSTKNISS   240
QTNLIPVKKE NYINDILLPP DFVYEKLGFV NSKKERLNAN LIFRIIKDFI KLPSAIKHYL   300
REK                                                                303

SEQ ID NO: 4            moltype = AA   length = 308
FEATURE                 Location/Qualifiers
source                  1..308
                        mol_type = protein
                        organism = Pasteurella sp.
SEQUENCE: 4
MNLIICCTPL QVLIAEKIIA KFPHTPFYGV MLSTVSNKKF DFYAKRLAQQ CQGFFSMVQH    60
KDRFNLLKEI LYLKRTFSGK HFDQVFVANI NDLQIQFLLS AIDFNLLNTF DDGTINIVPN   120
SLFYQDDPAT LQRKLINVLL GNKYSIQSLR ALSHTHYTIY KGFKNIIERV KPIELVAADN   180
SEKVTSAVIN VLLGQPVFAE DERNIALAER VIKQFNIHYY LPHPREKYRL AQVNYIDTEL   240
IFEDYILQQC QTHKYCVYTY FSSAIINIMN KSDNIEVVAL KIDTENPAYD ACYDLFDELG   300
VNVIDIRE                                                           308

SEQ ID NO: 5            moltype = AA   length = 342
FEATURE                 Location/Qualifiers
source                  1..342
                        mol_type = protein
                        organism = Neisseria meningitidis
SEQUENCE: 5
MERNAVSLLK EKLFNEEGEP VNLIFCYTIL QMKVAERIMA QHPGERFYVV LMSENRNEKY    60
DYYFNQIKDK AERAYFFHLP YGLNKSFNFI PTMAELKVKS MLLPKVKRIY LASLEKVSIA   120
AFLSTYPDAE IKTFDDGTGN LIQSSSYLGD EFSVNGTIKR NFARMMIGDW SIAKTRNASD   180
EHYTIFKGLK NIMDDGRRKM TYLPLFDASE LKTGDETGGT VRILLGSPDK EMKEISEKAA   240
KNFKIQYVAP HPRQTYGLSG VTTLNSPYVI EDYILREIKK NPHTRYEIYT FFSGAALTMK   300
DFPNVHVYAL KPASLPEDYW LKPVYALFTQ SGIPILTFDD KN                     342

SEQ ID NO: 6            moltype = AA   length = 272
FEATURE                 Location/Qualifiers
source                  1..272
                        mol_type = protein
                        organism = Pasteurella multocida
SEQUENCE: 6
MDKFAEHEIP KAVIVAGNGE SLSQIDYRLL PKNYDVFRCN QFYFEERYFL GNKIKAVFFT    60
PGVFLEQYYT LYHLRKNNEY FVDNVILSSF NHPTVDLEKS QKIQALFIDV INGYEKYLSK   120
LTAFDVYLRY KELYENQRIT SGVYMCAVAI AMGYTDIYLT GIDFYQASEE NYAFDNKKPN   180
IIRLLPDFRK EKTLFSYHSK DIDLEALSFL QQHYHVNFYS ISPMSPLSKH FPIPTVEDDC   240
ETTFVAPLKE NYINDILLPP HFVYEKLGTI VS                                272

SEQ ID NO: 7            moltype = AA   length = 388
FEATURE                 Location/Qualifiers
source                  1..388
                        mol_type = protein
                        organism = Pasteurella multocida
SEQUENCE: 7
MKTITLYLDP ASLPALNQLM DFTQNNEDKT HPRIFGLSRF KIPDNIITQY QNIHFVELKD    60
NRPTEALFTI LDQYPGNIEL NIHLNIAHSV QLIRPILAYR FKHLDRVSIQ QLNLYDDGSM   120
EYVDLEKEEN KDISAEIKQA EKQLSHYLLT GKIKFDNPTI ARYVWQSAFP VKYHFLSTDY   180
FEKAEFLQPL KEYLAENYQK MDWTAYQQLT PEQQAFYLTL VGFNDEVKQS LEVQQAKFIF   240
TGTTTWEGNT DVREYYAQQQ LNLLNHFTQA EGDLFIGDHY KIYFKGHPRG GEINDYILNN   300
AKNITNIPAN ISFEVLMMTG LLPDKVGGVA SSLYFSLPKE KISHIIFTSN KQVKSKEDAL   360
NNPYVKVMRR LGIIDESQVI FWDSLKQL                                     388

SEQ ID NO: 8            moltype = AA   length = 410
FEATURE                 Location/Qualifiers
source                  1..410
                        mol_type = protein
                        organism = Avibacterium avium
SEQUENCE: 8
MKQFDVYLDY ATLPSLNMMF DLVEKKDNQQ IERIIGFERF NLSEDKLSAF PQGKISFSKV    60
SLKDFTAFSD LLVNKIAQSD ELVELFIHTN LDHSFYNLPN VLEKLSPIAN KPTIKHLYLY   120
DDGSMNYKDL YEHREQDIKK LLASSQNELA KKLASHSNNN ELDSISRYTW HKFFPTDYIL   180
LRPDYLTIDE KMQPLKEFIG NNVSAMSWSR FEKLSPEQKT LFLKLVNVDE NTLHKLKNNS   240
EERTFIFTGT TTWEKDKDKR LANAKTQVVK LEDFLKPDGK FYLGNKIKVF FKGHPKGDEI   300
```

```
NEYILKQTGA ENIPANIPFE VLMMTNSLPD YVGGIMSSMY FSLPATHINK VIFLDSDKVK    360
NKNDAKAQTL SKLMLMLNVI TPEQIAFEEI PETKKNSFFK QAFDTLRSKF               410

SEQ ID NO: 9            moltype = AA  length = 312
FEATURE                 Location/Qualifiers
source                  1..312
                        mol_type = protein
                        organism = Mannheimia sp.
SEQUENCE: 9
MNLIICCTPL QVLIAEKILE IHRNEQFFGV MLSTVKNAKF DFYQSRLAKK CQQFFAMQQH    60
SERIQLLKEI IYLKSTFGGK KFNKVFLANI NELEIQFLLS AINFNEINTF DDGIANIVQS    120
GIFYKQECSG INRKLINTFL GNRYSLEKLK KLSKKHYTIY KGFPNIIENT VYIELINSTT    180
LPDSELNNSE VVNILLGQPI FERDDEKNII LAEKVIRQFN IDRYFPHPRE KYQISNVEYI    240
KTNLILEDYL FQECSDKKCR VYTYFSSAVI NILNKSPNIE VVALRVNVDN PTYIESYVLL    300
ENLGINIIDI RE                                                        312

SEQ ID NO: 10           moltype = AA  length = 300
FEATURE                 Location/Qualifiers
source                  1..300
                        mol_type = protein
                        organism = Campylobacter subantarcticus
SEQUENCE: 10
MQGGGNAIIC GNGPSLKDID YKKLPRKYDV FRCNQFYFEE KYYLGKNIKY AFFNPFVFFE    60
QYYTTKKLIE KKEYNIENII CSTFNLPTVD NENFIKNFNN YFCDAYLGHE ILHNIKDFLA    120
FIKYNELYEN NRITSGIYMC AIAIALGYKN IYLCGIDFYN DKNNMYGFDN KKENLLKLNP    180
EFLKKDSVYT KHSKEFDLKA LEFLKEIYGV NFYSLNNNEL SKYIPLAPNT NNNFVLIDKD    240
KNYVNDILIP KEKDYCKLFK QEDGKIKLKE NVYYKLFKDL FRLPSDIKHY LKEKYANKNR    300

SEQ ID NO: 11           moltype = AA  length = 302
FEATURE                 Location/Qualifiers
source                  1..302
                        mol_type = protein
                        organism = Campylobacter coli
SEQUENCE: 11
MQNVIIAGNG PSLQSINYQR LPKEYDIFRC NQFYFEDKYY LGKNIKAAFF NPYPFLQQYH    60
TAKQLVFNNE YKIENIFCST FNLPFIEKDN FINKFYDFFP DAKLGHKIIE NLKEFYAYIK    120
YNEIYLNKRI TSGIYMCAIA IALGYKNIYL CGIDFYEGET IYPFKAMSKN IKKIFPWIKD    180
FNPSNFHSKE YDIEILKLLE SIYKVNIYAL CDNSALANYF PLLVNTDNSF VLENKSDDCI    240
NDILLTNNTP GINFYKSQIQ VNNTEILLLN FQNMISAKEN EISNLNKILQ DSYKTINTKE    300
NE                                                                   302

SEQ ID NO: 12           moltype = AA  length = 259
FEATURE                 Location/Qualifiers
source                  1..259
                        mol_type = protein
                        organism = Campylobacter jejuni
SEQUENCE: 12
MKKVIIAGNG PSLKEIDYSR LPNDFDVFRC NQFYFEDKYY LGKKCKAVFY NPILFFEQYY    60
TLKHLIQNQE YETELIMCSN YNQAHLENEN FVKTFYDYFP DAHLGYDFFK QLKDFNAYFK    120
FHEIYFNQRI TSGVYMCAVA IALGYKEIYL SGIDFYQNGS SYAFDTKQKN LLKLAPNFKN    180
DNSHYIGHSK NTDIKALEFL EKTYKIKLYC LCPNSLLANF IELAPNLNSN FIIQEKNNYT    240
KDILPSSEA YGKFSKNIN                                                  259

SEQ ID NO: 13           moltype = DNA  length = 300
FEATURE                 Location/Qualifiers
misc_feature            1..300
                        note = Promoter sequence
source                  1..300
                        mol_type = other DNA
                        organism = synthetic construct
SEQUENCE: 13
gcggcacgcc ttgcagatta cggtttgcca cactttcat ccttctcctg gtgacataat     60
ccacatcaat cgaaaatgtt aataaatttg ttgcgcgaat gatctaacaa acatgcatca    120
tgtacaatca gatggaataa atggcgcgat aacgctcatt ttatgacgag gcacacacat    180
tttaagttcg atatttctcg tttttgctcg ttaacgataa gtttacagca tgcctacaag    240
catcgtggag gtccgtgact tcacgcata caacaaacat taaccaagga ggaaacagct     300

SEQ ID NO: 14           moltype = DNA  length = 300
FEATURE                 Location/Qualifiers
misc_feature            1..300
                        note = Promoter sequence
source                  1..300
                        mol_type = other DNA
                        organism = synthetic construct
SEQUENCE: 14
gcggcacgcc ttgcagatta cggtttgcca cactttcat ccttctcctg gtgacataat     60
ccacatcaat cgaaaatgtt aataaatttg ttgcgcgaat gatctaacaa acatgcatca    120
tgtacaatca gatggaataa atggcgcgat aacgctcatt ttatgacgag gcacacacat    180
tttaagttcg atatttctcg tttttgctcg ttaacgataa gtttacagca tgcctacaag    240
```

```
catcgtggag gtccgtgact ttcacgcata caacaaacat taaccaaatt cgaaacagct    300

SEQ ID NO: 15           moltype = DNA   length = 300
FEATURE                 Location/Qualifiers
misc_feature            1..300
                        note = Promoter sequence
source                  1..300
                        mol_type = other DNA
                        organism = synthetic construct
SEQUENCE: 15
gcggcacgcc ttgcagatta cggtttgcca cactttcat ccttctcctg gtgacataat     60
ccacatcaat cgaaatgtt aataaatttg ttgcgcgaat gatctaacaa acatgcatca    120
tgtacaatca gatggaataa atggcgcgat aacgctcatt ttatgacgag gcacacacat   180
tttaagttcg atatttctcg ttttgctcg ttaacgataa gttacagca tgcctacaag     240
catcgtggag gtccgtgact ttcacgcata caacaaacat taaccaagaa caaaacagct   300

SEQ ID NO: 16           moltype = DNA   length = 300
FEATURE                 Location/Qualifiers
misc_feature            1..300
                        note = Promoter sequence
source                  1..300
                        mol_type = other DNA
                        organism = synthetic construct
SEQUENCE: 16
gcggcacgcc ttgcagatta cggtttgcca cactttcat ccttctcctg gtgacataat     60
ccacatcaat cgaaatgtt aataaatttg ttgcgcgaat gatctaacaa acatgcatca    120
tgtacaatca gatggaataa atggcgcgat aacgctcatt ttatgacgag gcacacacat   180
tttaagttcg atatttctcg ttttgctcg ttaacgataa gttacagca tgcctacaag     240
catcgtggag gtccgtgact ttcacgcata caacaaacat taaccaagag caaaacagct   300

SEQ ID NO: 17           moltype = DNA   length = 107
FEATURE                 Location/Qualifiers
source                  1..107
                        mol_type = other DNA
                        organism = Escherichia coli
SEQUENCE: 17
tgtgagttag ctcactcatt aggcacccca ggctttacac tttatgcttc cggctcgtat     60
gttgtgtgga attgtgagcg gataacaatt tcacacagga aacagct                 107

SEQ ID NO: 18           moltype = DNA   length = 141
FEATURE                 Location/Qualifiers
misc_feature            1..141
                        note = Promoter sequence
source                  1..141
                        mol_type = other DNA
                        organism = synthetic construct
SEQUENCE: 18
tgtgagttag ctcactcatt aggcacccca ggctttacac tttatgcttc cggctcgtat     60
gttgtgtgga atgcctacaa gcatcgtgga ggtccgtgac tttcacgcat acaacaaaca   120
ttaaccaagg aggaaacagc t                                             141

SEQ ID NO: 19           moltype = DNA   length = 203
FEATURE                 Location/Qualifiers
misc_feature            1..203
                        note = Promoter sequence
source                  1..203
                        mol_type = other DNA
                        organism = synthetic construct
SEQUENCE: 19
tgcgtcgcca ttctgtcgca acacgccaga atgcggcggc gatcactaac tcaacaaatc     60
aggcgatgta accgctttca atctgtgagt gatttcacag tatcttaaca atgtgatagc   120
tatgattgca ccgtgcctac aagcatcgtg gaggtccgtg actttcacgc atacaacaaa   180
cattaacaaa aaccggagat acc                                           203

SEQ ID NO: 20           moltype = DNA   length = 203
FEATURE                 Location/Qualifiers
misc_feature            1..203
                        note = Promoter sequence
source                  1..203
                        mol_type = other DNA
                        organism = synthetic construct
SEQUENCE: 20
tgcgtcgcca ttctgtcgca acacgccaga atgcggcggc gatcactaac tcaacaaatc     60
aggcgatgta accgctttca atctgtgagt gatttcacag tatcttaaca atgtgatagc   120
tatgattgca ccgtgcctac aagcatcgtg gaggtccgtg actttcacgc atacaacaaa   180
cattaaccaa ggaggaaaca gct                                           203

SEQ ID NO: 21           moltype = DNA   length = 203
FEATURE                 Location/Qualifiers
```

| | | |
|---|---|---|
| misc_feature | 1..203 | |
| | note = Promoter sequence | |
| source | 1..203 | |
| | mol_type = other DNA | |
| | organism = synthetic construct | |

SEQUENCE: 21

```
tgcgtcgcca ttctgtcgca acacgccaga atgcggcggc gatcactaac tcaacaaatc   60
aggcgatgta accgctttca atctgtgagt gatttcacag tatcttaaca atgtgatagc  120
tatgattgca ccgtgcctac aagcatcgtg gaggtccgtg actttcacgc atacaacaaa  180
cattaaccaa ctaggaaaca gct                                          203
```

| | | |
|---|---|---|
| SEQ ID NO: 22 | moltype = DNA length = 203 | |
| FEATURE | Location/Qualifiers | |
| misc_feature | 1..203 | |
| | note = Promoter sequence | |
| source | 1..203 | |
| | mol_type = other DNA | |
| | organism = synthetic construct | |

SEQUENCE: 22

```
tgcgtcgcca ttctgtcgca acacgccaga atgcggcggc gatcactaac tcaacaaatc   60
aggcgatgta accgctttca atctgtgagt gatttcacag tatcttaaca atgtgatagc  120
tatgattgca ccgtgcctac aagcatcgtg gaggtccgtg actttcacgc atacaacaaa  180
cattaaccaa gagaaaaaca gct                                          203
```

| | | |
|---|---|---|
| SEQ ID NO: 23 | moltype = DNA length = 906 | |
| FEATURE | Location/Qualifiers | |
| source | 1..906 | |
| | mol_type = other DNA | |
| | organism = Campylobacter lari | |

SEQUENCE: 23

```
atggttggtg gtggtaatgc agttatttgt ggtaatggtc cgagcctgaa aaacatcgat   60
tataaacgtc tgccgaaaga attcgacgtg tttaaatgca accagttcta tttcgaggat  120
cgctattttg tgggcaagaa catcaaatat gccttttttca atccgttcgt gttcttcgag  180
cagtattata ccagcaaaaa gctgattcag aacggcagca atatcatcga aaatattgtg  240
tgcagcacct ttaatctgcc gctgattgat aacgagaact tcattaaact gttcccgagc  300
tatttttgtg atgcactgct gggtcatgaa gtgctggcca aaatcaatga tttctttgcc  360
ttcgtgaagt acaacgagat ctatgaaaat aaacgtatca ccagcggcat ctatatgtgt  420
gccgcagcag ttgcactggg ctataaaaac atttatctga ccgcatcga tttctacgac  480
gacaaaaata acatgtatgc cttcgaaagc aagcagcata atattctgag cctgctgccg  540
aacttcaaaa acaaagatag cgtttatgaa gcccacagca aaaactttga tctgaaaacc  600
ctgatctttc tgaaagaaaa atacaacgtg aacttttatg ccctgaatga aaatagcccg  660
atcagcaaat atatcgatct ggcaccgatt gaaaactcca actttatcct gaaagataaa  720
ccgagcaact acatcaacga tattctgatt ccgaacagca agtacaagaa caccatctga  780
aaagtgcaga accaggacag caaactgaaa cagaacatct actacaaact gttcaaggac  840
ctgtttcatc tgccgagcga tattaaacat tatcttaaag agaaatacgc caacaaaaat  900
cgctaa                                                             906
```

| | | |
|---|---|---|
| SEQ ID NO: 24 | moltype = DNA length = 1080 | |
| FEATURE | Location/Qualifiers | |
| source | 1..1080 | |
| | mol_type = other DNA | |
| | organism = Neisseria gonorrhoeae | |

SEQUENCE: 24

```
atgatcttct ataccttga tcgcgtgaat cagggtgaac gtaatgcagt tagcctgctg   60
aaagataaac tgtttaacga agaaggcaaa ccggtcagtc tgatcttttg ttataccatc  120
ctgcagatga aagtggccga acgtattatg gcacagcatc cgggtgaacg cttttatgtt  180
gttctgatga gcgaaaaccg caacgagaaa tatgattact actttaacca gatcaaggac  240
aaagcagaac gtgcctattt cttttatctg ccgtatggtc tgaacaaaag ctttaacttt  300
attccgacca tggccgagct gaaagttaaa agcatgctgc tgccgaaagt gaaacgtatt  360
tatctggcaa gcctggaaaa agttagcatt gcagcatttc tgagcaccta tccggatgca  420
gaaatcaaaa cctttgatga tggcaccaat aacctgattc gtgaaagcag ctatttaggt  480
ggtgaatttg cagttaatgg tgcgatcaaa cgtaattttg cacgtatgat ggttggcgat  540
tggagcattg caaaaacccg taatgcatcc gatgaacact ataccatctt taaaggcctg  600
aagaacatta tggatgatgg tcgtcgtaaa atgacctatc tgccgctgtt tgatgcaagc  660
gaactgaaag ccggtgatga aaccggtggc accgttcgta ttctgctggg tagtccggat  720
aaagaaatga agaaattag cgagaaagca gccaaaaact tcaacattca gtatgttgca  780
ccgcatccgc gtcagaccta tggtctgtca ggtgttaccg cactgaatag cccgtatgtg  840
attgaagatt atattctgcg cgagatcaaa aagaatccgc atacacgtta tgagatctac  900
accttttca gcggtgcagc actgaccatg aaagattttc cgatgttca tgtgtatgca  960
ctgaaaccgg caagtctgcc ggaagattat tggctgaaac tgtttatgc actgttttcgt 1020
caggcagata ttccgattct ggcattcgat gataaaaatc agagccacgg taaaagcaaa 1080
```

| | | |
|---|---|---|
| SEQ ID NO: 25 | moltype = DNA length = 912 | |
| FEATURE | Location/Qualifiers | |
| source | 1..912 | |
| | mol_type = other DNA | |
| | organism = Pasteurella oralis | |

SEQUENCE: 25

```
atggatgaag ttgaacgtag ccgtgaatgt aaaagcgttg ttgttgcagg taatggtgca   60
```

```
agtctgaccc aggttgatta tagcctgctg ccggttaatt atgatgtgtt tcgttgcaac    120
cagttctatt tcgaggatca ttattttctg ggcaaaaaga tcaaagcagc ctttttttaca   180
ccgggtgttc tgctggaaca gtattacacc ctgtatcatc tgcgcaaaaa caacgaatat    240
agcgtggata aaatcatcct gagcagcttt aatcatccga ccgttgatct gagcaaaagc    300
gagaatatca aaaagctgtt catcgatgtg atcaacgaat cctgagcaaa              360
ctgagcgatt tcgatattta tctgcgctac aaagaactgt atgaaagcca gcgtattacc    420
agcggcattt atatgtgtgc agttgcaatt gccatgggct ataccgatat ctatctgacc    480
ggtatcgatt tctatgagag caacagcaaa agctatgcct tgaaccgaa aaagaccaac    540
attattagtc tgctgcccga cttttaaaaac atcagcagca aatttcacta ccacaacaaa   600
gatgcagatc tggaagcact gtattttctg caaaaaaact acagcgtgaa cttttacagc    660
attagtccgg gttcactgct gtatgaacat tttccgacca gcaccaaaaa cattagctca    720
cagaccaatc tgattccggt gaagaaagag aactatatca cgatattct gctgcctccg    780
gatttcgttt atgaaaaact gggttttgtg aatagcaaaa aagaacgcct gaatgccaac    840
ctgattttcc gcattatcaa agactttatc aaactgccga gcgccatcaa acattatctg    900
cgtgaaaaat aa                                                        912

SEQ ID NO: 26           moltype = DNA  length = 1029
FEATURE                 Location/Qualifiers
source                  1..1029
                        mol_type = other DNA
                        organism = Neisseria meningitidis
SEQUENCE: 26
atggaacgta acgccgtgag cctgctgaaa gaaaaactgt ttaacgaaga aggtgaaccg     60
gtcaatctga tcttctgcta taccattctg cagatgaaag tggcagaacg tattatggct    120
caacatccgg gcgaacgctt ttatgtggtt ctgatgagtg aaaaccgtaa cgaaaaatac    180
gattactact tcaaccagat caaagacaaa gcagaacgc cttatttctt tcacctgccg     240
tacgtctga acaaatcgtt taatttcatt ccgacgatgg cggaactgaa agttaaaagc    300
atgctgctgc cgaaagtcaa acgtatctat ctggcatccc tggaaaaagt gtcaattgcg    360
gcctttctgt ccacctaccc ggatgctgaa atcaaaacct tcgatgacgg cacggggtaac   420
ctgattcaaa gctctagtta tctgggcgat gaatttttcg ttaacggtac gatcaaacgt    480
aatttcgccc gcatgatgat cggcgattgg tctattgcga aaacccgcaa cgccagtgac    540
gaacattaca cgatcttcaa aggcctgaaa aacatcatgg atgacggtcg tcgcaaaatg    600
acctacctgc cgctgttcga tgccagcgaa ctgaaacgg gcgacgaaac cggcggtacg    660
gttcgtattc tgctgggttc cccggataaa gaaatgaaag aaatctcaga aaaagcagct    720
aaaaacttca aaatccagta tgtcgcaccg cacccgcgcc aaaacctacgg tctgtcggt    780
gtgaccacgc tgaacagccc gtatgttatt gaagattaca cctgcgtgta aattaagaaa    840
aacccgcata cccgctatga aatctacacg ttttctctg gtgcggccct gaccatgaaa    900
gattttccga atgtccacgt gtatgcgctg aaaccggcca gtctgccgga agactactgg   960
ctgaaaccgg tgtacgctct gttcacgcaa tccggcatcc cgattctgac ctttgacgat   1020
aaaaactaa                                                           1029

SEQ ID NO: 27           moltype = DNA  length = 927
FEATURE                 Location/Qualifiers
source                  1..927
                        mol_type = other DNA
                        organism = Pasteurella sp.
SEQUENCE: 27
atgaacctga ttatttgttg tacaccgctg caggttctga ttgccgaaaa gattattgca    60
aaatttccgc acacaccgtt ttatggtgtt atgctgagca ccgttagcaa caaaaagttt    120
gatttttatg ccaaacgtct ggcacagcag tgtcagggtt tctttagcat ggttcagcat    180
aaagatcgct tcaacctgct gaaagaaatt ctgtatctga aacgtacctt tagcggcaaa    240
catttttgatc aggttttttgt ggccaacatc aatgacctgc agattcagtt tctgctgagc    300
gccattgatt ttaatctgct gaataccttt gatgatggca ccattaacat tgttccgaac    360
agcctgtttt atcaggatga tccggcaaca ctgcagcgta aactgattaa tgttctgctg    420
ggtaacaaat acagcattca gagccgtgct gcactggttca ataccatta taccatctat    480
aaaggcttca aaaacatcat cgaacgcgtg aaaccgattg aactggttgc agcagataat    540
tcagaaaaag ttaccagcgc agttattaac gtgctgctgg ccagccggt tttttgcagaa    600
gatgaacgta atattgcact ggccgaacgt gttatcaaac agtttaacat ccattactat    660
ctgccgcatc cgcgtgaaaa aatcgtctg gcccaggtta actatattga taccgaactg    720
atcttcgagg attattatct gcagcagtgc cagacacaca aatattgcgt ttatacctat    780
tttagcagcg cgatcatcaa catcatgaac aaaaagcgata acattgaagt ggtggccctg    840
aaaattgata cagaaaatcc ggcatatgat gcctgctatg acctgtttga tgaactgggt    900
gttaacgtga ttgatatccg cgaataa                                        927

SEQ ID NO: 28           moltype = DNA  length = 819
FEATURE                 Location/Qualifiers
source                  1..819
                        mol_type = other DNA
                        organism = Pasteurella multocida
SEQUENCE: 28
atggataaaat ttgccgaaca tgaaattccg aaagccgtta ttgttgcagg taatggtgaa     60
agcctgagcc agattgatta tcgtctgctg ccgaaaaact atgatgtgtt tcgttgcaac    120
cagttctatt tcgaagaacg ctattttctg ggcaacaaaa tcaaagccgt gttttttaca    180
ccgggtgttc tgctggaaca gtattacacc ctgtatcatc tgaaacgcaa caacgaatat    240
ttcgtggata atgtgattct gagcagcttt aatcatccga ccgttgatct ggaaaaaagc    300
cagaaaattc aggcccgtgtt tatcgatgtg attaacggct atgaaagta cctgagcaaa    360
ctgaccgcat ttgatgttta tctgcgctat aaagaactgt atgaaaacca gcgtattacc    420
agcggtgttt atatgtgtgc agttgcaatt gccatgggct ataccgatat ttatctgacc    480
ggtatcgatt tttatcaggc cagcgaagaa aactatgcct tcgataacaa aaagccgaac    540
```

-continued

```
attattcgcc tgctgcctga ttttcgtaaa gaaaaaaccc tgtttagcta ccacagcaaa  600
gatatcgatc tggaagcact gagctttctg cagcagcatt atcatgttaa cttctatagc  660
attagcccga tgagtccgct gagtaaacat tttccgattc cgaccgtgga agatgattgt  720
gaaaccacct ttgttgcacc gctgaaagag aactatatta acgatattct gctgcctccg  780
cacttcgttt atgaaaaact gggcaccatt gtgagctaa                         819

SEQ ID NO: 29          moltype = DNA  length = 1167
FEATURE                Location/Qualifiers
source                 1..1167
                       mol_type = other DNA
                       organism = Pasteurella multocida
SEQUENCE: 29
atgaaaacca ttacgctgta tttagatccg gcaagcctgc ctgcactgaa ccagctgatg  60
gattttaccc agaataacga ggataaaacc catccgcgta tctttggtct gagccgcttt  120
aaaatcccgg ataacattat tacccagtac cagaacatcc acttcgtgga actgaaagat  180
aatcgtccga ccgaagcact gtttaccatt ctggatcagt atccgggtaa tatcgaactg  240
aacatccatc tgaatattgc ccatagcgtt cagctgattc gtccgattct ggcatatcgt  300
tttaaacatc tggatcgtgt tagcattcag cagctgaacc tgtatgatga tggtagcatg  360
gaatatgtgg atctggaaaa agaagagaac aaagatatca gcgcagaaat caaacaggca  420
gaaaaacagc tgagccatta tctgctgacc ggcaaaatta agtttgataa tccgaccatt  480
gcgcgttatg tttggcagag cgcatttccg gttaaatatc attttctgag caccgactat  540
ttcgagaaag cagaatttct gcagccgctg aaagaatatc tggcagaaaa ttaccagaaa  600
atggattgga ccgcatatca gcaactgaca ccggaacagc aggcatttta tctgaccctg  660
gttggtttta acgatgaagt taaacagagc ctggaagttc agcaggccaa atttatcttt  720
accggcacca ccacctggga aggtaatacc gatgttcgtg aatattatgc acagcaacag  780
ctgaatctgc tgaatcattt tacacaggcc gaaggtgacc tgtttattgg tgatcattac  840
aaaatctatt tcaaaggtca tccgcgtggt ggcgaaatta atgattatat tctgaacaac  900
gccaaaaaca tcaccaacat tccggcaaac attagctttg aagttctgat gatgaccggt  960
ctgctgccgg ataaagttgg tggtgttgca agcagcctgt attttagcct gccgaaagaa  1020
aaaatcagcc acatcatttt caccagcaac aaacaggtga aaagcaaaga agatgcactg  1080
aataacccgt acgttaaagt tatgcgtcgt ctgggtatta ttgatgaaag ccaggttatc  1140
ttttgggaca gcctgaaaca gctgtaa                                      1167

SEQ ID NO: 30          moltype = DNA  length = 1233
FEATURE                Location/Qualifiers
source                 1..1233
                       mol_type = other DNA
                       organism = Avibacterium avium
SEQUENCE: 30
atgaaacagt tcgatgtgta tctggattat gcaaccctgc cgagcctgaa tatgatgttt  60
gatctggttg agaaaaagga caaccagcag attgaacgca ttattggttt tgaacgcttt  120
aacctgagcg aggataaact gagcgcattt ccgcagggta aaattagctt tagcaaagtg  180
agcctgaaag attttaccgc atttagcgac ctgctggtta acaaaattgc acagagtgat  240
gaactggtgg aactgtttat tcataccaat ctggatcaca gcttttacaa tctgccgaat  300
gttctggaaa aactgagccc gattgcaaac aaatttacca tcaaacacct gtacctgtat  360
gacgatggta gcatgaacta taaagatctg tatgaacacc gcgagcagga tattaagaaa  420
ctgctggcaa gcagccagaa tgaactggca aagaaactgg caagccatag caataataac  480
gaactggata gcattagccg ttatacctgg cataaattct ttccgaccga ttatattctg  540
ctgcgtccgg attatctgac cattgatgag aaaatgcagc cgctgaaaga attcattggt  600
aataatgtta gcgccatgag ctggtcacgt tttgaaaaac tgtcaccgga acagaaaacc  660
ctgtttctga aactggttaa cgtggatgaa aacaccctgc acaaactgaa aaataatagc  720
gaagaacgca cctttatctt taccggcacc accacctggg aaaaagacaa agataaacgt  780
ctggcaaatg cgaaaaccca ggtgaaagtt ctggaagatt tcctgaaacc ggatggcaaa  840
ttctatctgg gcaataaaat caaagtgttc ttcaaaggtc acccgaaagg cgacgaaatt  900
aatgagtata ttctgaaaca gaccggtgcc gaaaatattc cggctaatat tccgtttgaa  960
gtgctgatga tgaccaatag cctgccggat tatgtaggtg gtattatgag cagcatgtat  1020
tttagcctgc ctgccacaca tattaacaaa gtgatttttc tggacagcga taaagtgaaa  1080
aacaagaatg atgcaaaagc acagaccctg agcaaactga tgctgatgtt aaatgttatt  1140
acccctgagc agatcgcctt tgaggaaatt ccggaaacca aaaagaacag cttctttaaa  1200
caggcctttg ataccctgcg tagcaaattt taa                               1233

SEQ ID NO: 31          moltype = DNA  length = 939
FEATURE                Location/Qualifiers
source                 1..939
                       mol_type = other DNA
                       organism = Mannheimia sp.
SEQUENCE: 31
atgaacctga ttatttgttg tacaccgctg caggttctga ttgcagagaa aattctggaa  60
attcaccgca acgaacagtt tttcggtgtt atgctgagca ccgttaaaaa cgccaaattc  120
gatttttatc agagccgtct ggcaaagaaa tgtcagcagt tctttgcaat gcagcagcat  180
agcgaacgta ttcagctgct gaaagaaatc atctatctga aagcacctt  cggtggcaaa  240
aagttcaata aagtttttct ggccaacatc aacgagctgg aaatccagtt tctgctgagc  300
gcaattaact ttaacgaaat caacaccttc gatgacggca ttgccaatat tgttcagagc  360
ggcattttct acaaacaaga atgcagcggt attaaccgca aactgattaa tacctttctg  420
ggcaatcgtt acagcctgga aaaactgaaa aagctgagca aaaagcacta taccatctat  480
aaaggcttcc cgaacattat cgaaaacacc gtgtatatcg aactgatcaa tagcaccaca  540
ctgccggata gcgaactgaa taatagcgaa gttgttaata ttctgctggg ccagccgatt  600
tttgaacgtg atgatgagaa aacattatc  ctggccgaaa aagtgattcg ccagtttaac  660
attgatcgct attttccgca tccgcgtgaa aaatatcaga ttagcaatgt cgagtatatc  720
```

```
aaaaccaacc tgatcctgga agattacctg tttcaagaat gtagcgataa aaagtgccgt    780
gtgtatacct atttagcag cgcagttatt aacatcctga acaaaagccc gaatattgaa    840
gttgttgcac tgcgtgttaa tgtggataat ccgacctata ttgaaagcta tgtgctgctg    900
gaaaatctgg gcattaacat tattgatatc cgcgaataa                          939
```

| SEQ ID NO: 32 | moltype = DNA length = 903 |
|---|---|
| FEATURE | Location/Qualifiers |
| source | 1..903 |
| | mol_type = other DNA |
| | organism = Campylobacter subantarcticus |

```
SEQUENCE: 32
atgcaaggtg gtggtaatgc cattatttgt ggtaatggtc cgagcctgaa agatatcgat     60
tataagaaac tgcctcgcaa gtatgatgtg tttcgttgca atcagttcta cttcgaggaa    120
aaatactacc tgggcaagaa catcaaatac gccttttca atccgttcgt gttcttcgaa    180
cagtattaca ccaccaaaaa gctgatcgag aagaaagagt ataacatcga gaacattatc    240
tgcagcacct ttaatctgcc gaccgtggat aatgaaaact tcatcaaaaa cttcaacaac    300
tatttttgcg acgcctatct gggtcatgaa attctgcata acatcaaaga ttttctggcc    360
tttatcaaat acaacgaact gtatgaaaac accgtatta ccagcggcat ttatatgtgt    420
gcaattgcca ttgcgctggg ctataaaaac atttatctgt gcggcatcga tttctataac    480
gataaaaaca acatgtacgg cttcgacaac aagaaagaaa tctgctgaa actgaacccg    540
gaattcctga aaaaggatag cgtttatacc agcacagca aagagtttga tctgaaagca    600
ctggaatttc tgaaagaaat ctatggcgtg aacttctaca ccgtgaataa taacgaactg    660
agcaaatata tcccgctggc accgaatacc aataataact ttgtgctgat cgacaaagat    720
aaaaactatg tgaacgacat tctgatcccg aaagagaaag attactgcaa gctgttcaaa    780
caagaggacg gtaaaatcaa gctgaaagag aacgtctact ataaactgtt caaagacctg    840
tttcgtctgc cgagcgatat taaacattac cttaaagaga gtacgccaa caagaaccgc    900
taa                                                                 903
```

| SEQ ID NO: 33 | moltype = DNA length = 909 |
|---|---|
| FEATURE | Location/Qualifiers |
| source | 1..909 |
| | mol_type = other DNA |
| | organism = Campylobacter coli |

```
SEQUENCE: 33
atgcagaatg ttattattgc aggtaatggt ccgagcctgc agagcattaa ctatcagcgt     60
ctgccgaaag aatatgatat tttccgttgc aaccagttct acttcgagga taaatactat    120
ctgggcaaga acattaaagc agcctttttt aacccgtatc cgtttctgca gcagtatcat    180
accgcaaaac agctggtttt taacaacgag tacaagatcg aaaacatctt ttgcagcacc    240
tttaacctgc cgtttatcga gaaagacaac ttcatcaaca agttctatga tttcttccg    300
gatgcaaaac tgggccataa aatcattgaa aacctgaaag agttctacgc ctacatcaaa    360
tacaacgaga tctatctgaa caaacgtatt ccagcggca tttatatgtg tgcaattgcc    420
attgcgctgg gctataaaaa catctatctg tgcggcatcg atttctatga ggcgaaacc    480
atttatccgt ttaaagccat gagcaaaaac atcaaaaaaa tctttccgtg gatcaaagac    540
ttcaacccga gcaattttca cagcaaagag tatgacatcg agatcctgaa actgctggaa    600
agcatcctata aagtgaacat ttatgccctg tgcgataata gcgcactggc aaactattt    660
ccgctgctgg ttaatacgga taatagcttt gttctggaaa acaaaagcga cgattgcatc    720
aatgatattc tgctgaccaa taatacccct ggcatcaact tctataaaag ccagattcag    780
gtgaacaaca ccgaaattct gctgctgaat tttcagaata tgatcagcgc caaagaaaac    840
gaaattagca acctgaacaa aattctgcag gacagctaca aaaaccatca accaaagag    900
aacgagtaa                                                           909
```

| SEQ ID NO: 34 | moltype = DNA length = 903 |
|---|---|
| FEATURE | Location/Qualifiers |
| source | 1..903 |
| | mol_type = other DNA |
| | organism = Campylobacter jejuni |

```
SEQUENCE: 34
atgacacgta cccgtatgga aaatgaactg attgtgagca aaaacatgca gaacattatc     60
attcaggta atggtccgag cctgaaaaac attaactata aacgtctgcc tcgcgagtat    120
gatgttttc gttgtaacca gttctacttc gaggacaaat attacctggg caaaaaatc    180
aaagccgtgt ttttcaatcc gggtgttttt ctgcagcagt atcataccgc aaaacagctg    240
attctgaaaa acgagtacga gatcaaaaac atcttttgca gcaccttaa cctgccgttt    300
attgaaagca acgatttcct gcaccagttt tacaactttt ttccggatgc aaaactgggc    360
tatgaagtga ttgaaaacct gaaagaattc tacgcctaca tcaagtcgag atcttgca    420
ttcaacaaac gcattaccag cggtgtttat atgtgtgcaa ttgccattgc gctgggctat    480
aaaccattt atctgtgcgg tatcgatttc tatgaaggcg acgttattta ccgtttgaa    540
gcaatgagca ccaacattaa acaatctttt ccgggtatca aagacttcaa accgagcaat    600
tgtcacagca agaatatga tattgaggcc tgaaactgc tgaaagcat ctataagtg    660
aacatctatg ccctgtgta tatagcatt tggcaaatc attttccgct gagcattaac    720
atcaacaaca actttaccct ggaaaacaag cacaacaaca gcattaatga tatcctgctg    780
accgataata caccgggtgt tagctttta aaaatcagc tgaaagccga taataagatc    840
atgctgaact tctacaacat cctgcatagc aaagacaacc tgatcaaatt cctgaacaaa    900
taa                                                                 903
```

| SEQ ID NO: 35 | moltype = DNA length = 2818 |
|---|---|
| FEATURE | Location/Qualifiers |
| source | 1..2818 |
| | mol_type = other DNA |
| | organism = Campylobacter jejuni |

```
SEQUENCE: 35
atgaaagaaa taaaaataca aaatataatc ataagtgaag aaaaagcacc cttagtcgta    60
cctgaaatag gcattaatca taatggcagt ttagaactag ctaaaattat ggtagatgca   120
gcctttagcg caggtgctaa gattataaag catcaaactc atattgttga agatgagatg   180
agtaaggccg ctaaaaaagt aattcctggt aatgcaaaaa taagcattta tgagattatg   240
caaaaatgtg ctttaggatta taaagatgag ctagcactta agaatacac agaaaaatta    300
ggtcttgttt atcttagcac acctttttct cgtgcaggtg cgaaccgctt agaagatatg   360
ggagttagtg cttttaagat tggttcaggt gagtgtaata attatccgct tattaaacac   420
atagcagcct ttaaaaagcc tatgatagtt agcacagtaa tgaatagtat tgaaagtata   480
aaaccaactg taaaaatctt attagacaat gaaattcctt ttgttttaat gcacacgacc   540
aatctttacc caaccccgca taatcttgta agattaaacg ctatgcttga gttaaaaaaa   600
gaattttctt gtatggtagg cttaagcgac cacacaacag ataatcttgc gtgtttaggt   660
gcagttgtac ttggagcttg tgtgcttgaa agacatttta ctgatagtat gcatagaagt   720
ggcctgata tagtttgttc tatggataca aaggcttaa aagagctaat tatacaagt    780
gagcaaatgg ctataataag aggaaataat gaaagtaaaa aagcggctaa acaagaacaa   840
gttacaattg attttgcctt tgcaagtgta gttagcatta agatattaa aaaaggcgaa    900
gttttatcta tggataatat ttgggttaaa agacctggac ttggtggaat tagtgcggct   960
gaatttgaaa atattttagg caaaaaagca ttaagagta tagaaaatga tgctcagtta   1020
agctatgagg attttgcgtg aaaaaaatcc tttttataac aggctctagg gctgattatt  1080
ctaagattaa atctttaatg tacagggtgc aaaactcaag cgaatttgaa ctttacatct  1140
ttgcaacagg aatgcactta agtaaaaatt ttggctatac agttaaagaa ctttataaaa  1200
atggctttaa aaatattat gaattataa attatgataa atattatcaa actgataagg   1260
ctttagctac tacaattgat ggattttcaa ggtatgcaaa tgagctaaaa cctgatttaa  1320
tcgtagtaca tggagataga attgagcctt agcagcagc tattgttgga gcattaaata    1380
atatcttagt agcgcatatt gaaggcggag agatttcagg aactattgac gatagcttac  1440
gccacgctat atcaaaacta gctcatattc atttagtaag tgatgagttt gcaaaaaggc   1500
gtttaatgca gcttggagaa gatgaaaaat ctattttttat cataggttcg cctgatttag   1560
aactttaaaa cgataaataaa atttcactta gcgaagcaaa aaaatattat gatataaatt   1620
atgaaaacta cgctttgctt atgtttcatc ctgttacaac tgaaattact agcattaaaa   1680
atcaagcaga caatttagta aaagcaagtga tacaaagtaa taaaaaattat attgttattt   1740
atccaaataa tgatttaggt tttgaattaa tcttgcaaag ctatgaagag tttaaaaata   1800
acctagatt taagcttttt ccatcgctta gatttgagta ttttataact ttgttaaaaa    1860
atgctgattt tataataggt aattcaagtt gtattttaaa agaggcctta tacttaaaaaa   1920
cagcagggat tttagttggc tcaagacaaa atggaagact tggcaatgaa aatacactaa    1980
aagttaatgc aaaatagtgat gaaatactaa aagctattaa cactattcat aaaaaacaag   2040
atttatttag cgctaagtta gagattttag atagctcaaa attattttt gaatattac    2100
aaagcggaga ttttttttaaa ctcagcacac aaaaagtttt taaggatata aatgagctt    2160
agcaataatc cctgctcgtg gtggctcaaa gggtattaaa aataactgca ctaaatgcta     2220
aaacaataaa cctttaattt actacacgat caaagctgca ctaaatgcta aaagcattag    2280
taaagttgtt gtaagcagtg atagtgatga aatttttaaat tatgcaaaaa gtcaaaatgt    2340
tgatattta aaacgcccaa ttagccttgc acaagatgat accacaagcg ataaagtgct    2400
gttacatgct ctaaaatttt ataaagatta tgaagatgta gttttttac aacccacttc    2460
accgctaaga acaaatattc atattaatga agctttaat ctttataaaa atagcaatgc    2520
aaatgcccta attagcgtaa gcgaatgtga taataaaatt ctaaaagcct ttgtttgtaa    2580
tgattgtggc gatttagcag ggatttgaa tgatgaatat ccttttatgc caaggcaaaa    2640
attgcctaaa acttatatga gcaatggtgc aatttatatt ttaaagataa agaattttt     2700
aaacaatcct agcttttttac aaagcaaaac caagcttttt ttaatggacg aaagctcaag   2760
tttagatatt gactgtttgg aggatttaaa aaaggttgaa cagatatgga aaaaataa      2818
SEQ ID NO: 36           moltype = AA  length = 332
FEATURE                 Location/Qualifiers
source                  1..332
                        mol_type = protein
                        organism = Neisseria meningitidis
SEQUENCE: 36
MQPLVSVLIC AYNVEKYFAQ SLAAVVNQTW RNLEILIVDD GSTDGTLAIA KDFQKRDSRI    60
KILAQAQNSG LIPSLNIGLD ELAKSGMGEY IARTDADDIA APDWIEKIVG EMEKDRSIIA   120
MGAWLEVLSE EKDGNRLARH HRHGKIWKKP TRPEDIADFF PFGNPIHNNT MIMRRSVIDG   180
GLRYNTERDW AEDYQFWYDV SKLGRLAYYP EALVKYRLHA NQVSSKYSIR QHEIAQGIQK   240
TARNDFLQSM GFKTRFDSLE YRQIKAVAYE LLEKHLPEED FERARRFLYQ CFKRTDTLPA   300
GAWLDFAADG RMRRLFTLRQ YFGILHRLLK NR                                 332

SEQ ID NO: 37           moltype = AA  length = 439
FEATURE                 Location/Qualifiers
source                  1..439
                        mol_type = protein
                        organism = Helicobacter pylori
SEQUENCE: 37
MISVYIISLK ESQRRLDTEK LVLESNEKFK GRCVFQIFDA ISPKHEDFEK FVQELYDSSS    60
LLKSDWFHSD YCYQELLPQE FGCYLSHYLL WKECVKLNQP VVILEDDVAL ESNFMQALED   120
CLKSPFDFVR LYGHYWGGHK TNLCALPVYT ETEEAEASIE KTPIENYEVT SPPPPNPTRD   180
TQQDFITETQ QDPKELSEPC KIAPQKISFN QVVFKKIKRK LNRFIGSILA RTEVYKNIVA   240
KYDDLTTKYD DLTTKYDDLT TKYDDLTTKY DDLNKNIAEK YDELMGKYES LLAKEVNIKE   300
TFWESRADSE KEALFLDHFY LTSVYVATTA GYYLTPKGAK TFIEATERFK IIEPVDMFIN   360
NPTYHDIANF TYVPCPVSLN KHAFNSTIQN AKKPDISLKP PKKSYFDNLF YHKFNARKCL   420
KAFNKYSKQY APLKTPKEV                                                439

SEQ ID NO: 38           moltype = AA  length = 394
FEATURE                 Location/Qualifiers
```

```
source                          1..394
                                mol_type = protein
                                organism = Rosenbergiella nectarea
SEQUENCE: 38
MQSFTPPAPK GGNPVFMMFM LVTFFVSIAG ALQAPTLSLY LSQELAAKPF MVGLFFTINA    60
VTGIIISFIL AKRSDRKGDR RRLLMFCCAM AIANALMFAF VRQYVVLITL GLILSALTSV   120
VMPQLFALAR EYADRTGREV VMFSSVMRTQ MSLAWVIGPP ISFALALNYG FITLYLVAAA   180
LFLLSLILIK TTLPSVPRLY PAEDLAKSAA SGWKRTDVRF LFAASVLMWV CNLMYIIDMP   240
LYISKSLGMP ESFAGVLMGT AAGLEIPVML LAGYLAKRVG KRPLVIVAAV CGLAFYPAML   300
VFHQQTGLLI IQLLNAVFIG IVAGLVMLWF QDLMPGKAGA ATTLFTNSVS TGMIFAGLCQ   360
GLLSDLLGHQ AIYVLATVLM VIALLLLLRV KEQA                              394

SEQ ID NO: 39                   moltype = AA   length = 393
FEATURE                         Location/Qualifiers
source                          1..393
                                mol_type = protein
                                organism = Yersinia bercovieri
SEQUENCE: 39
MKSALTFSRR INPVFLAFFV VAFLSGIAGA LQAPTLSLFL STEVKVRPLW VGLFYTVNAI    60
AGITVSFILA KRSDSRGDRR KLIMVCYLMA VGNCLLFAFN RDYLTLITAG VLLASVANTA   120
MPQIFALARE YADSSAREVV MFSSIMRAQL SLAWVIGPPL SFMLALNYGF TLMFSIAAGI   180
FVLSALVVWF ILPSVPRAEP VVDAPVVVQG SLFADKNVLL LFIASMLMWT CNTMYIIDMP   240
LYITASLGLP ERLAGLLMGT AAGLEIPIML LAGYSVRYFG KRKIMLFAVL AGVLFYTGLV   300
LFKFKTALML LQIFNAIFIG IVAGIGMLYF QDLMPGRAGA ATTLFTNSIS TGVILAGVLQ   360
GGLTETWGHD SVYVMAMVLS ILALIICARV REA                               393

SEQ ID NO: 40                   moltype = AA   length = 393
FEATURE                         Location/Qualifiers
source                          1..393
                                mol_type = protein
                                organism = Yersinia frederiksenii
SEQUENCE: 40
MKSALTFSRR INPVFLAFFV VAFLSGIAGA LQAPTLSLFL STEVKVRPLW VGLFYTVNAI    60
AGITVSFVLA KRSDLRGDRR KLILVCYLMA VGNCLLFAFN RDYLTLITAG VLLAAVANTA   120
MPQIFALARE YADNSAREVV MFSSIMRAQL SLAWVIGPPL SFMLALNYGF TLMFCIAAGI   180
FVLSALVVWF ILPSVQRAEP VMDAPTVAQG SLFADKDVLL LFIASMLMWT CNTMYIIDMP   240
LYITASLGLP ERLAGLLMGT AAGLEIPIML LAGYSVRRFG KRKIMLFAVL AGVLFYTGLV   300
LFKFKSALML LQIFNAIFIG IVAGIGMLYF QDLMPGRAGA ATTLFTNSIS TGVILAGVLQ   360
GVLTETWGHN SVYVMAMILA ILSLIICARV REA                               393

SEQ ID NO: 41                   moltype = DNA   length = 203
FEATURE                         Location/Qualifiers
misc_feature                    1..203
                                note = Promoter Sequence
source                          1..203
                                mol_type = other DNA
                                organism = synthetic construct
SEQUENCE: 41
tgcgtcgcca ttctgtcgca acacgccaga atgcggcggc gatcactaac tcaacaaatc    60
aggcgatgta accgctttca atctgtgagt gatttcacag tatcttaaca atgtgatagc   120
tatgattgca ccgtgcctac aagcatcgtg gaggtccgtg actttcacgc atacaacaaa   180
cattaaccaa aggaaaaaca gct                                          203

SEQ ID NO: 42                   moltype = DNA   length = 203
FEATURE                         Location/Qualifiers
misc_feature                    1..203
                                note = Promoter Sequence
source                          1..203
                                mol_type = other DNA
                                organism = synthetic construct
SEQUENCE: 42
tgcgtcgcca ttctgtcgca acacgccaga atgcggcggc gatcactaac tcaacaaatc    60
aggcgatgta accgctttca atctgtgagt gatttcacag tatcttaaca atgtgatagc   120
tatgattgca ccgtgcctac aagcatcgtg gaggtccgtg actttcacgc atacaacaaa   180
cattaaccaa ctgagaaaca gct                                          203

SEQ ID NO: 43                   moltype = DNA   length = 203
FEATURE                         Location/Qualifiers
misc_feature                    1..203
                                note = Promoter Sequence
source                          1..203
                                mol_type = other DNA
                                organism = synthetic construct
SEQUENCE: 43
tgcgtcgcca ttctgtcgca acacgccaga atgcggcggc gatcactaac tcaacaaatc    60
aggcgatgta accgctttca atctgtgagt gatttcacag tatcttaaca atgtgatagc   120
tatgattgca ccgtgcctac aagcatcgtg gaggtccgtg actttcacgc atacaacaaa   180
cattaaccaa ccgagaaaca gct                                          203
```

| SEQ ID NO: 44 | moltype = DNA   length = 310 |
| --- | --- |
| FEATURE | Location/Qualifiers |
| misc_feature | 1..310 |
| | note = Promoter Sequence |
| source | 1..310 |
| | mol_type = other DNA |
| | organism = synthetic construct |

SEQUENCE: 44
```
atgcgcaaat gcggcacgcc ttgcagatta cggtttgcca cacttttcat ccttctcctg   60
gtgacataat ccacatcaat cgaaaatgtt aataaatttg ttgcgcgaat gatctaacaa  120
acatgcatca tgtacaatca gatggaataa atgcgcgat aacgctcatt ttatgacgag   180
gcacacacat tttaagttcg atatttctcg tttttgctcg ttaacgataa gtttacagca  240
tgcctacaag catcgtggag gtccgtgact ttcacgcata caacaaacat taaccaacta  300
ggaaacagct                                                         310
```

| SEQ ID NO: 45 | moltype = DNA   length = 203 |
| --- | --- |
| FEATURE | Location/Qualifiers |
| misc_feature | 1..203 |
| | note = Promoter Sequence |
| source | 1..203 |
| | mol_type = other DNA |
| | organism = synthetic construct |

SEQUENCE: 45
```
tgcgtcgcca ttctgtcgca acacgccaga atgcggcggc gatcactaac tcaacaaatc   60
aggcgatgta accgctttca atctgtgagt gatttcacag tatcttaaca atgtgatagc  120
tatgattgca ccgtgcctac aagcatcgtg gaggtccgtg actttcacgc atacaacaaa  180
cattaaccaa gagcaaaaca gct                                          203
```

| SEQ ID NO: 46 | moltype = DNA   length = 189 |
| --- | --- |
| FEATURE | Location/Qualifiers |
| misc_feature | 1..189 |
| | note = Promoter Sequence |
| source | 1..189 |
| | mol_type = other DNA |
| | organism = synthetic construct |

SEQUENCE: 46
```
gaaacattc ataaattaaa tgtgaattgc cgcacacatt attaaataag atttacaaaa    60
tgttcaaaat gacgcatgaa atcacgtttc actttcgaat tatgagcgaa tatgcgcgat  120
gcctacaagc atcgtggagg tccgtgactt tcacgcatac aacaaacatt aaccaaggag  180
gaaacagct                                                          189
```

| SEQ ID NO: 47 | moltype = DNA   length = 239 |
| --- | --- |
| FEATURE | Location/Qualifiers |
| misc_feature | 1..239 |
| | note = Promoter Sequence |
| source | 1..239 |
| | mol_type = other DNA |
| | organism = synthetic construct |

SEQUENCE: 47
```
ccatttagcc atagtaaaaa catgaattgt tgatttcgc gcatattcgc tcataattcg    60
aaaagtgaaac gtgatttcat gcgtcatttt gaacattttat taaatcttat ttaataatgt 120
gtgcggcaat tcacatttaa tttatgaatg ttttcttaac atcgcggcat gcctacaagc  180
atcgtggagg tccgtgactt tcacgcatac aacaaacatt aaccaaggag gaaacagct   239
```

| SEQ ID NO: 48 | moltype = DNA   length = 310 |
| --- | --- |
| FEATURE | Location/Qualifiers |
| misc_feature | 1..310 |
| | note = Promoter Sequence |
| source | 1..310 |
| | mol_type = other DNA |
| | organism = synthetic construct |

SEQUENCE: 48
```
atgcgcaaat gcggcacgcc ttgcagatta cggtttgcca cacttttcat ccttctcctg   60
gtgacataat ccacatcaat cgaaaatgtt aataaatttg ttgcgcgaat gatctaacaa  120
acatgcatca tgtacaatca gatggaataa atgcgcgat aacgctcatt ttatgacgag   180
gcacacacat tttaagttcg atatttctcg tttttgctcg ttaacgataa gtttacagca  240
tgcctacaag catcgtggag gtccgtgact ttcacgcata caacaaacat taaccaactg  300
agaaacagct                                                         310
```

| SEQ ID NO: 49 | moltype = DNA   length = 310 |
| --- | --- |
| FEATURE | Location/Qualifiers |
| misc_feature | 1..310 |
| | note = Promoter Sequence |
| source | 1..310 |
| | mol_type = other DNA |
| | organism = synthetic construct |

SEQUENCE: 49
```
atgcgcaaat gcggcacgcc ttgcagatta cggtttgcca cacttttcat ccttctcctg   60
gtgacataat ccacatcaat cgaaaatgtt aataaatttg ttgcgcgaat gatctaacaa  120
```

```
acatgcatca tgtacaatca gatggaataa atggcgcgat aacgctcatt ttatgacgag    180
gcacacacat tttaagttcg atatttctcg tttttgctcg ttaacgataa gtttacagca    240
tgcctacaag catcgtggag gtccgtgact tcacgcata caacaaacat taaccaaccg    300
agaaacagct                                                          310

SEQ ID NO: 50            moltype = DNA  length = 310
FEATURE                  Location/Qualifiers
misc_feature             1..310
                         note = Promoter Sequence
source                   1..310
                         mol_type = other DNA
                         organism = synthetic construct
SEQUENCE: 50
atgcgcaaat gcggcacgcc ttgcagatta cggtttgcca cactttcat ccttctcctg    60
gtgacataat ccacatcaat cgaaaatgtt aataaatttg ttgcgcgaat gatctaacaa   120
acatgcatca tgtacaatca gatggaataa atggcgcgat aacgctcatt ttatgacgag   180
gcacacacat tttaagttcg atatttctcg tttttgctcg ttaacgataa gtttacagca   240
tgcctacaag catcgtggag gtccgtgact tcacgcata caacaaacat taaccaagag   300
aaaaacagct                                                          310

SEQ ID NO: 51            moltype = DNA  length = 350
FEATURE                  Location/Qualifiers
misc_feature             1..350
                         note = Promoter Sequence
source                   1..350
                         mol_type = other DNA
                         organism = synthetic construct
SEQUENCE: 51
tgcgtcgcca ttctgtcgca acacgccaga atgcggcggc gatcactaac tcaacaaatc    60
aggcgatgta accgctttca atctgtgagt gatttcacag tatcttaaca atgtgatagc   120
tatgattgca ccgttttaac gttgtaaccc gtatgtaaca gtgaataatc acttttgccg   180
aggtaacagc gtcataacaa caattaaagc cgttttctgg agcgttaccg ggcatggaag   240
aacgaatttt aaaagtgagt cttcggcgtt cagtaacact tcattaactc tactgccccg   300
ccgagcattt atctcaagca ctaccctgca taagcaagga ggaaacagct              350

SEQ ID NO: 52            moltype = DNA  length = 310
FEATURE                  Location/Qualifiers
misc_feature             1..310
                         note = Promoter Sequence
source                   1..310
                         mol_type = other DNA
                         organism = synthetic construct
SEQUENCE: 52
atgcgcaaat gcggcacgcc ttgcagatta cggtttgcca cactttcat ccttctcctg     60
gtgacataat ccacatcaat cgaaaatgtt aataaatttg ttgcgcgaat gatctaacaa   120
acatgcatca tgtacaatca gatggaataa atggcgcgat aacgctcatt ttatgacgag   180
gcacacacat tttaagttcg atatttctcg tttttgctcg ttaacgataa gtttacagca   240
tgcctacaag catcgtggag gtccgtgact tcacgcata caacaaacat taaccaaagg   300
aaaaacagct                                                          310

SEQ ID NO: 53            moltype = DNA  length = 310
FEATURE                  Location/Qualifiers
misc_feature             1..310
                         note = Promoter Sequence
source                   1..310
                         mol_type = other DNA
                         organism = synthetic construct
SEQUENCE: 53
atgcgcaaat gcggcacgcc ttgcagatta cggtttgcca cactttcat ccttctcctg     60
gtgacataat ccacatcaat cgaaaatgtt aataaatttg ttgcgcgaat gatctaacaa   120
acatgcatca tgtacaatca gatggaataa atggcgcgat aacgctcatt ttatgacgag   180
gcacacacat tttaagttcg atatttctcg tttttgctcg ttaacgataa gtttacagca   240
tgcctacaag catcgtggag gtccgtgact tcacgcata caacaaacat taaccaagag   300
ctaaacagct                                                          310

SEQ ID NO: 54            moltype = DNA  length = 189
FEATURE                  Location/Qualifiers
misc_feature             1..189
                         note = Promoter Sequence
source                   1..189
                         mol_type = other DNA
                         organism = synthetic construct
SEQUENCE: 54
gaaaacattc ataaattaaa tgtgaattgc cgcacacatt attaaataag atttacaaaa    60
tgttcaaaat gacgcatgaa atcacgtttc actttcgaat tatgagcgaa tatgcgcgat   120
gcctacaagc atcgtggagg tccgtgactt tcacgcatac aacaaacatt aaccaaggag   180
gaaacagct                                                           189
```

SIALYLTRANSFERASES FOR IN VIVO SYNTHESIS OF 3'SL

CROSS-REFERENCE TO RELATED APPLICATIONS

This application claims priority to Denmark Application No. PA 202270077, filed on Mar. 2, 2022, the contents of which are fully incorporated herein by reference.

SEQUENCE LISTING

The instant application contains a Sequence Listing which has been submitted in ST.26 XML format via Patent Center and is hereby incorporated by reference in its entirety. Said ST.26 XML copy, created on Aug. 22, 2023, is named "032991-8003 Sequence Listing.xml", and is 82,675 bytes in size.

FIELD

The present disclosure relates to the production of sialylated Human Milk Oligosaccharides (HMOs), in particular to the biosynthetic production of 3'-sialyllactose (3'SL), and to genetically engineered cells suitable for use in said production.

BACKGROUND

The design and construction of bacterial cell factories to produce sialylated Human Milk Oligosaccharides (HMOs), especially more complex sialylated Human Milk Oligosaccharides (HMOs), is of paramount importance to provide innovative and scalable solutions for the more complex products of tomorrow.

To this end, rational strain engineering principles are commonly applied to single bacterial cells. Such principles usually refer to a) the introduction of a desired biosynthetic pathway to the host, b) the increase of the cellular pools of relevant activated sugars required as donors in the desired reactions, c) the enhancement of lactose import by the native lactose permease LacY and d) the introduction of suitable glycosyltransferases to facilitate the biosynthetic production of sialylated oligosaccharides (for review see Bych et al 2019, Current Opinion in Biotechnology 56:130-137).

WO2007/101862 discloses production of sialylated HMOs using e.g., the alpha-2,3-sialyltransferase, Nst, from *Neisseria meningitidis* in combination with expression of the neuBCA genes to produce CMP-neu5AC.

Further attempts to produce sialylated HMOs are presented in WO2019/020707, which describes a number of sialyltransferases which are capable of producing complex sialylated HMOs in a cell, wherein 3'SL could hypothetically be produced as a minor biproduct.

Schelch et al 2020, Biotechnology Advances 44, 107613, is a review on bacterial sialyltransferases properties. Table 2 summarizes bacterial sialyltransferases expressed in *E. coli*, with no indication of what sialyloligosaccharides were produced if any.

Production of sialylated HMOs, can be hampered by side-activities of the sialyltransferases in the production strain, which may affect the ability of the cell to grow robustly even in the absence of substrate which is in turn reflected in poor yields of the sialylated HMO product.

In summary, sialyltransferases for HMO production that enable a higher yield of sialylated product, as well as a stable growth of the production strain, are needed to obtain a robust sialylated HMO production platform that is scalable for industrial production of sialylated HMOs, in particular of 3'SL.

SUMMARY

The present disclosure relates to a genetically modified cell comprising a recombinant nucleic acid sequence encoding an enzyme with α-2,3-sialyltransferase activity, capable of producing sialylated HMOs, in particular 3'SL at a high yield, while maintaining a stable growth of the production strain in large scale. In particular the stable growth is observed across a wider range of growth rates during product formation, which in turn allows for a faster as well as for a larger variation in feeding the carbon source during the fermentation.

In particular, the present disclosure relates to a genetically modified cell overexpressing a α-2,3-sialyltransferase selected from the group consisting of Clari1, Neigon, Poral, and PmN, comprising or consisting of the amino acid sequence of one of the SEQ ID NOs: 1, 2, 3 or 4 or an amino acid sequence with at least 80%, such as at least 85%, 90%, 95% or 99% identity to one of the SEQ ID NOs: 1, 2, 3 or 4. Preferably, the genetically modified cell exhibits stable growth, when the selected α-2,3-sialyltransferase is expressed under control of a strong and preferably heterologous promotor, as well as a high product yield, and is thus suitable for large-scale industrial production of sialylated HMOs. The sialylated HMO produced by the cell of the present disclosure is typically selected from the group consisting of 3'SL, FSL, DSLNT and LST-a. Preferably the sialylated HMO produced is 3'SL, in particular 3'SL without the presence of other HMO by-products.

The genetically modified cell according to the present disclosure can further comprise a promoter element that controls the expression of the recombinant nucleic acid encoding an enzyme with α-2,3-sialyltransferase activity. The sialyltransferase may e.g., be under the control of a promoter selected from the group consisting of PglpF, PglpA, PglpT, Plac, PmgIB and variants thereof with a nucleic acid sequence selected from the group consisting of SEQ ID NOs 12-22 or 41-54, respectively. Preferably, the sialyltransferase is under the control of a recombinant promoter, which is stronger than the native *E. coli* Plac promoter. Preferably, the sialyltransferase is under the control of a recombinant promoter selected from the group consisting of SEQ ID NOs 13, 18, 19, 20, 21, 22, 41, 42, 43, 44, 45, 46, 47, 48, 49, 50 and 51.

The present disclosure further relates to a nucleic acid construct comprising a recombinant nucleic acid sequence encoding an enzyme with α-2,3-sialyltransferase activity, wherein said enzyme is selected from the group of sialyltransferases consisting of Clari1 comprising or consisting of the amino acid sequence of SEQ ID NO: 1 or an amino acid sequence with at least 80%, such as at least 85%, such as at least 90%, such as at least 95% identity to SEQ ID NO: 1, Neigon comprising or consisting of the amino acid sequence of SEQ ID NO: 2 or an amino acid sequence with at least 80%, such as at least 85%, such as at least 90%, such as at least 95% identity to SEQ ID NO: 2, Poral comprising or consisting of the amino acid sequence of SEQ ID NO: 3 or an amino acid sequence with at least 80%, such as at least 85%, such as at least 90%, such as at least 95% identity to SEQ ID NO: 3 and PmN comprising or consisting of the amino acid sequence of SEQ ID NO: 4 or an amino acid sequence with at least 80%, such as at least 85%, such as at least 90%, such as at least 95% identity to SEQ ID NO: 4 and wherein said nucleic acid sequence is under control of a promoter sequence selected from the group consisting of PglpF, PglpA, PglpT, Plac, PmglB and variants thereof, with the nucleic acid sequences according to SEQ ID NOs 12-22 or 41-54]. Said nucleic acid construct is typically used in a host cell for producing a sialylated HMO, such as 3'SL.

The genetically modified cell according to the present disclosure can further comprise a nucleic acid sequence encoding an MFS transporter protein capable of exporting the sialylated HMO into the extracellular medium. Preferably, the MFS transporter protein is the Nec, YberC or Fred protein, with an amino acid sequence according to SEQ ID NOs: 38, 39 or 40, respectively.

The genetically modified cell according to the present disclosure can comprise a biosynthetic pathway for making a sialic acid sugar nucleotide, such as CMP-Neu5Ac. Said sialic acid sugar nucleotide pathway can be encoded by the nucleic acid sequence encoding NeuBCA from *Campylobacter jejuni* (SEQ ID NO:35). The nucleic acid sequence encoding NeuBCA, can be encoded from a high-copy plasmid bearing the neuBCA operon.

The genetically modified cell according to the present disclosure can be a microorganism, such as a bacterium or a fungus, wherein said fungus can be selected from a yeast cell, such as of the genera Komagataella, *Kluyveromyces, Yarrowia, Pichia, Saccaromyces, Schizosaccharomyces* or *Hansenula*, or from a filamentous fungous of the genera *Aspargillus, Fusarium* or *Thricoderma*, and said bacterium can be selected from the exemplified group consisting of *Escherichia* sp., *Bacillus* sp., *lactobacillus* sp. and *Campylobacter* sp. Accordingly, the genetically modified cell according to the present disclosure can be *E coli*.

The genetically modified cell of the present disclosure can be used in the production of a sialylated HMO, in particular 3'SL, at a high yield, while maintaining a stable growth.

Accordingly, the present disclosure also relates to a method for producing a sialylated human milk oligosaccharide (HMO), in particular 3'-SL, said method comprising culturing a genetically modified cell comprising a recombinant nucleic acid sequence encoding an enzyme with α-2,3-sialyltransferase activity, wherein said enzyme is selected from the group consisting of Clari1, Neigon, Poral and PmN, comprising or consisting of the amino acid sequence of one of the SEQ ID NOs: 1, 2, 3 or 4 or an amino acid sequence with at least 80%, such as at least 85%, 90%, 95% or 99% identity to one of the SEQ ID NOs: 1, 2, 3 or 4. In some embodiments, said genetically modified cell comprises at least one additional modification according to the present disclosure.

Various exemplary embodiments and details are described hereinafter, with reference to the figures and sequences when relevant. It should be noted that the figures are only intended to facilitate the description of the embodiments. They are not intended as an exhaustive description of the disclosure or as a limitation on the scope of the disclosure. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

BRIEF DESCRIPTION OF THE FIGURES

FIG. 3A) shows the carbon dioxide evolution rate (Cer) of the strains during the fermentation. FIG. 3B) shows the reflection from the same fermentation during the time of fermentation.

DETAILED DESCRIPTION

Figure 1:
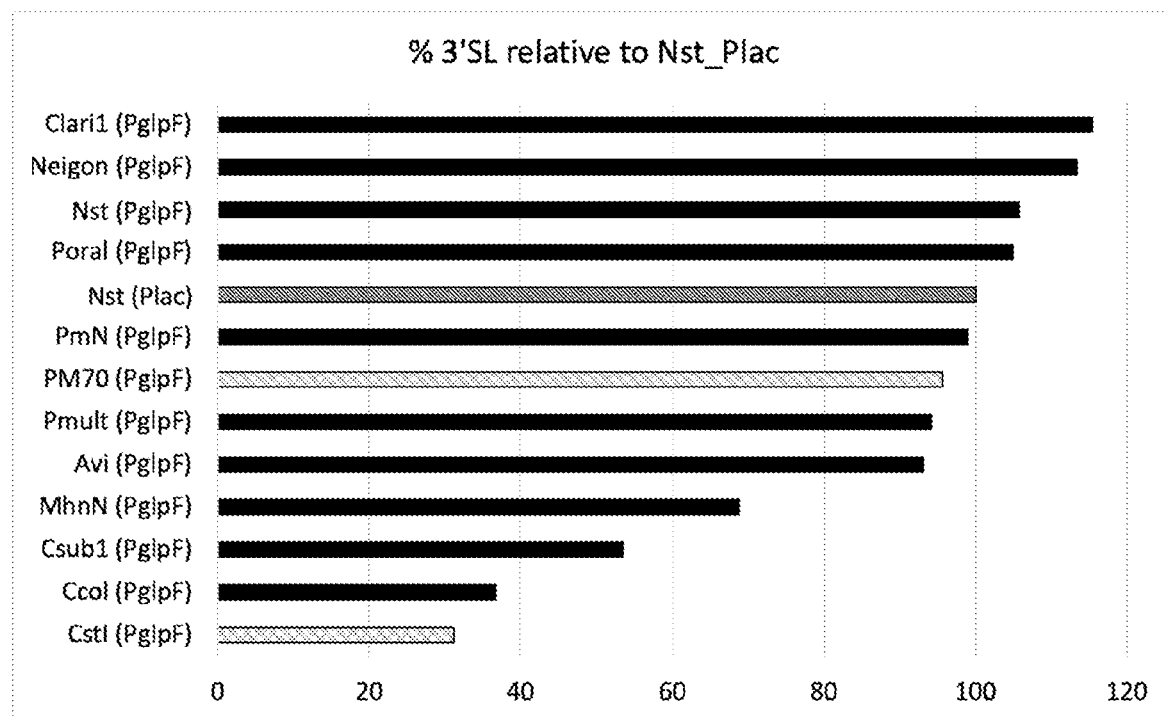
FIG. 1: Percentage, %, of 3'SL molar content (mM) in strains expressing a given α-2,3-sialyltransferase activity relative to the molar content of cells expressing Nst under the control of the Plac promoter (hatched bar). Cstl and PM70, are known in the prior art to be able to produce 3'SL and are indicated by dotted bars.

The present disclosure approaches the biotechnological challenges of in vivo HMO production, in particular of sialylated HMOs that contain at least one sialyl monosaccharide, such as the sialylated HMOs 3'SL, FSL and LST-a. The present disclosure offers specific strain engineering solutions to produce specific sialylated HMOs, in particular 3'SL, by exploiting the substrate specificity towards the terminal galactose moiety on lactose and activity of the α-2,3-sialyltransferases of the present disclosure, which improves the production of sialylated HMOs, both in terms of strain stability in large-scale fermentations and increased production yields.

In other words, a genetically modified cell covered by the present disclosure expresses genes encoding key enzymes for sialylated HMO biosynthesis, in some embodiments along with one or more genes encoding a biosynthetic pathway for making a sialic acid sugar nucleotide, such as the neuBCA operon from *Campylobacter jejuni* shown in SEQ ID NO: 35, which enables the cell to produce a sialylated oligosaccharide from substrates, such as lactose and nucleotide-activated sugars, such as in particular CMP-N-acetylneuraminic acid.

In particular, the sialylated HMO(s) produced is selected from the group consisting of 3'SL, FSL, DSLNT and LST-a, and presently preferred, the sialylated HMO produced is 3'SL. To produce, FSL, DSLNT and LST-a the genetically modified cell, requires the presence of additional glycosyltransferases such as β-1,3-N-acetyl-glucosaminyl-transferase and β-1,3-galactosyltransferase to produce LST-a from lactose as initial substrate, or a α-1,3-fucosyltransferase to produce FSL.

The advantage of using any one of the α-2,3-sialyltransferases of the present disclosure in the present context is their ability to recognize and sialylate lactose specifically to generate 3'SL as the only HMO when starting from lactose as the initial substrate and being capable of being expressed from a strong promoter while maintaining stable growth of the production strain. The enzymes presented here not only provide high 3'SL titers, but they also provide a stable growth that reaches a high growth density. Examples of strains that exhibit a stable growth by reaching a high growth density are provided in example 1. In particular, the present disclosure describes α-2,3-sialyltransferases which produce higher titers of 3'SL than α-2,3-sialyltransferases described in the prior art, such as Cstl and PM70 (see WO2019/020707) and/or exhibits a higher or similar growth density than Cstll and/or Nst (see WO2007/101862) used in the same host cell under the same growth conditions. The traits of the α-2,3-sialyltransferases described herein are therefore well-suited for large-scale industrial production of 3'SL.

The genetically modified cells of the present disclosure, which express an α-2,3-sialyltransferase of the present disclosure, enable the production of high titers of 3'SL while maintaining or improving a stable growth of said genetically modified cell when compared to the α-2,3-sialyltransferase Nst (SEQ ID NO: 5). Thereby, the present disclosure enables a more efficient 3'SL production, which is highly beneficial in biotechnological production of simple sialylated HMOs, such as 3'SL.

As shown in example 1, the genetically modified cells of the present disclosure form 3'SL at a level that is at least equal to, or at least 5%, such as 10% above the level of 3'SL formed by a Nst_plac strain, a PM70 strain or a Cstl strain under the same growth conditions. In particular, strains expressing Clari1, Poral, Neigon or PmN, produced more than 3-times as much 3'SL as Cstl expressing strains under the same conditions.

The optical density (OD) shown in Example 1 suggests that overexpression of Nst using the heterologous PglpF promoter instead of the Plac promoter is indeed affecting the growth of the cells, which is not the case to the same extent for any of the sialyltransferases of the present disclosure under the heterologous PglpF promoter, thus making it possible to use these sialyltransferases more effectively in industrial scale production of sialylated HMOs, such as 3'SL.

In the following sections, individual elements of the disclosure and in, particular of the genetically modified cell is described, it is understood that these elements can be combined across the individual sections.

Oligosaccharides

In the present context, the term "oligosaccharide" means a sugar polymer containing at least three monosaccharide units, i.e., a tri-, tetra-, penta-, hexa- or higher oligosaccharide. The oligosaccharide can have a linear or branched structure containing monosaccharide units that are linked to each other by interglycosidic linkages. Particularly, the oligosaccharide comprises a lactose residue at the reducing end and one or more naturally occurring monosaccharides of 5-9 carbon atoms selected from aldoses (e.g., glucose, galactose, ribose, arabinose, xylose, etc.), ketoses (e.g., fructose, sorbose, tagatose, etc.), deoxysugars (e.g. rhamnose, fucose, etc.), deoxy-aminosugars (e.g. N-acetyl-glucosamine, N-acetyl-mannosamine, N-acetyl-galactosamine, etc.), uronic acids and ketoaldonic acids (e.g. N-acetyl-neuraminic acid). Preferably, the oligosaccharide is an HMO.

Human Milk Oligosaccharide (HMO) Preferred oligosaccharides of the disclosure are human milk oligosaccharides (HMOs).

The term "human milk oligosaccharide" or "HMO" in the present context means a complex carbohydrate found in human breast milk. The HMOs have a core structure comprising a lactose unit at the reducing end that can be elongated by one or more beta-N-acetyl-lactosaminyl and/or one or more beta-lacto-N-biosyl unit, and this core structure can be substituted by an alpha-L-fucopyranosyl and/or an alpha-N-acetyl-neuraminyl (sialyl) moiety. HMO structures are e.g., disclosed by Xi Chen in Chapter 4 of Advances in Carbohydrate Chemistry and Biochemistry 2015 vol 72.

The present disclosure focuses on sialylated HMO's, which are generally acidic. Examples of acidic HMOs include 3'-sialyllactose (3'SL), 6'-sialyllactose (6'SL), 3-fucosyl-3'-sialyllactose (FSL), 3'-O-sialyllacto-N-tetraose a (LST-a), fucosyl-LST-a (FLST-a), 6'-O-sialyllacto-N-tetraose b (LST-b), fucosyl-LST b (FLST b), 6'-O-sialyllacto-N-neotetraose (LST-c), fucosyl-LST-c (FLST-c), 3'-O-sialyllacto-N-neotetraose (LST-d), fucosyl-LST d (FLST-d), sialyl-lacto-N-hexaose (SLNH), sialyl-lacto-N-neohexaose I (SLNH-I), sialyl-lacto-N-neohexaose II (SLNH-II) and disialyl-lacto-N-tetraose (DSLNT).

In one aspect of the present disclosure, the sialylated human milk oligosaccharide (HMO) produced by the cell is a sialylated HMO selected from the group consisting of 3'SL, FSL, DSLNT and LST-a. In a further aspect of the present disclosure, the sialylated human milk oligosaccharide (HMO) produced by the cell is an HMO of three monosaccharide units, such as 3'SL.

Production of some of these HMO's may require the presence of two or more glycosyltransferase activities, in particular if starting from lactose as the acceptor oligosaccharide. This is however not the case for the production for 3'SL, which only requires expression of one glycosyltransferase with α-2,3-sialyltransferase activity.

An Acceptor Oligosaccharide

A genetically modified cell according to the present disclosure comprises a recombinant nucleic acid sequence encoding an enzyme with α-2,3-sialyltransferase activity capable of transferring sialic acid from an activated sugar to the terminal galactose of an acceptor oligosaccharide.

In the context of the present disclosure, an acceptor oligosaccharide is an oligosaccharide that can act as a substrate for a glycosyltransferase capable of transferring a glycosyl moiety from a glycosyl donor to the acceptor oligosaccharide. The glycosyl donor is preferably a nucleotide-activated sugar as described in the section on "glycosyltransferases". Preferably, the acceptor oligosaccharide is a precursor for making an HMO and can also be termed the precursor molecule.

In the present context, said acceptor oligosaccharide is preferably lactose for the production of 3'SL. The production of more complex HMOs than 3'SL, such as LST-a or FSL may also include more complex acceptor molecules such as lacto-N-neotetraose (LNT), which is produced from the precursor molecules lactose and/or lacto-N-triose II (LNT-II) or 3FL. In both cases, the precursor molecule can be fed to the genetically modified cell which is capable of producing the sialylated HMO from the precursor or the cell can be modified to produce the more complex acceptor molecule from lactose.

The acceptor oligosaccharide can be either an intermediate product of the present fermentation process, an end-product of a separate fermentation process employing a separate genetically modified cell, or an enzymatically or chemically produced molecule.

Glycosyltransferases

The genetically modified cell according to the present disclosure comprises at least one recombinant nucleic acid sequence encoding at least one glycosyltransferase capable of transferring a sialyl residue from a sialyl donor to an acceptor oligosaccharide to synthesize a sialylated human milk oligosaccharide product, i.e., a sialyltransferase.

The genetically modified cell, according to the present disclosure may comprise at least one further recombinant nucleic acid sequence encoding at least one glycosyltransferase capable of transferring a glycosyl residue from a glycosyl donor to an acceptor oligosaccharide. The additional glycosyltransferase(s) can enable the genetically modified cell to synthesize LNT from a precursor molecule, such as lactose or LNT-II, or to synthesize 3FL from lactose. The additional glycosyltransferase may also be capable of further decorating e.g., a 3'SL molecule to generate for example FSL or an LST-a or LST-b molecule to generate DSLNT.

The additional glycosyltransferase is preferably selected from the group consisting of, fucosyltransferases, galactosyltransferases, glucosaminyltransferases, sialyltransferases, and N-acetylglucosaminyl transferases.

Where it is desired to produce more complex HMOs the α-2,3-sialyltransferase described herein may be combined with one or more glycosyltransferases selected from the group consisting of β-1,3-galactosyltransferases, β-1,4-galactosyltransferases and β-1,3-N-acetyl-glucosaminyl-transferases. In specific embodiments the additional glycosyltransferase may be a β-1,3-galactosyltransferase, or a β-1,4-galactosyltransferase, or a combination of a β-1,3-galactosyltransferase and a β-1,3-N-acetyl-glucosaminyl-transferases, or combination of a β-1,4-galactosyltransferase and a β-1,3-N-acetyl-glucosaminyl-transferase. In a further embodiment a fucosyltransferase selected from the group consisting of α-1,2-fucosyltransferases, α-1,3-fucosyltransferase, and α-1,3/4-fucosyltransferase may be introduced onto the genetically engineered cell described herein.

In one aspect, the sialyltransferase in the genetically modified cell of the present disclosure is an α-2,3-sialyltransferase. Preferably, the α-2,3-sialyltransferase is capable of transferring a sialic acid unit onto the terminal galactose of a lactose molecule. Preferably, solely at the C3 position of the galactose, thereby generating 3'SL as the only HMO when starting from lactose as initial substrate.

In the present disclosure, the at least one functional enzyme (α-2,3-sialyltransferase) capable of transferring a sialyl moiety from a sialyl donor to an acceptor oligosaccharide can be selected from the list consisting of Clari1, Neigon, Poral and PmN (table 1). These enzymes, once expressed in a genetically modified cell can e.g., be used to produce 3'SL.

In an embodiment, the expression of an α-2,3-sialyltransferase of the disclosure is further combined with a β-1,3-galactosyltransferase, such as galTK from *Helicobacter pylori* (SEQ ID NO: 37, or a functional variant thereof). In a further embodiment, a third enzyme is added, such as a β-1,3-N-acetyl-glucosaminyl-transferase, e.g., LgtA from *Neisseria meningitidis* (SEQ ID NO: 36, or a functional variant thereof).

Exemplified glycosyltransferases are preferably selected from the glycosyltransferases described below.

α-2,3-sialyltransferase

An alpha-2,3-sialyltransferase refers to a glycosyltransferase that catalyzes the transfer of sialyl from a donor substrate, such as CMP-N-acetylneuraminic acid, to an acceptor molecule in an alpha-2,3-linkage. Preferably, an alpha-2,3-sialyltransferase used herein does not originate in the species of the genetically engineered cell, i.e., the gene encoding the alpha-2,3-sialyltransferase is of heterologous origin and is selected from an alpha-2,3-sialyltransferase identified in table 1. Heterologous alpha 2,3-sialyltransferases that are capable of transferring a sialyl moiety onto lactose are known in the art, three of which are identified in table 1.

The α-2,3-sialyltransferases investigated in the present application are listed in table 1. The sialyltransferase can be selected from an amino acid sequence with at least 80%, such as 80%, such as at least 90%, such as at least 95%, or such as at least 99% identity to the amino acid sequence of any one of the alpha-2,3-sialyltransferases listed in table 1.

TABLE 1

List of alpha-2,3-sialyltransferase enzymes capable of producing 3'SL.

| Enzyme Name | GenBank ID | SEQ ID NO: | Origin | Ref |
|---|---|---|---|---|
| Clari1 | EGK8106227.1 | 1 | *Campylobacter lari* | |
| Neigon | AAW89748.1 | 2 | *Neisseria gonorrhoeae* FA 1090 | |
| Poral | WP_101774487.1 | 3 | *Pasteurella oralis* | |
| PmN | WP_005726268.1 | 4 | *Pasteurella* (multispecies) | |
| Nst | AAC44541.1 | 5 | *Neisseria meningitidis* MC58 | WO2007/101862 |
| PM70 | AAK03258.1 | 6 | *Pasteurella multocida* subsp. Pm70 | WO2019/020707 |
| Pmult | WP_005753497.1 | 7 | *Pasteurella multocida* | |
| Avi | WP_115249238.1 | 8 | *Avibacterium avium* | |
| MhnN | WP_176810284.1 | 9 | *Mannheimia* (multispecies) | |
| Csub1 | WP_039664428.1 | 10 | *Campylobacter subantarcticus* | |
| Ccol | WP_075498955.1 | 11 | *Campylobacter coli* | |
| Cstl | AAF13495.1 | 12 | *Campylobacter jejuni* | WO2019/020707 |

The GenBank IDs reflect the full-length enzymes, in the present disclosure truncated or mutated versions may have been used, these are represented by SEQ ID NOs.

The alpha-2,3-sialyltransferases Nst, PM70 and Cstl are known from the prior art as alpha-2,3-sialyltransferases that can produce sialylated HMOs.

Example 1 of the present disclosure has identified the heterologous alpha-2,3-sialyltransferases Clari1, Neigon and Poral (SEQ ID NO: 1, 2 and 3, respectively), which are capable of producing higher or equal 3'SL titers when introduced into a genetically modified cell, than the known alpha-2,3-sialyltransferases Nst, PM70 and Cstl.

Example 1 of the present disclosure further has identified that the heterologous alpha-2,3-sialyltransferases Clari1, Neigon, Poral and PmN (SEQ ID NO: 1, 2, 3 and 4 respectively), are capable of producing similar or higher 3'SL titers when introduced into a genetically modified cell, than the known alpha-2,3-sialyltransferases Nst, PM70 and Cstl, while not significantly affecting the growth of the genetically modified cell.

In one embodiment of the disclosure, the enzyme with α-2,3-sialyltransferase activity is Clari1 from *Campylobacter lan* comprising or consisting of the amino acid sequence of SEQ ID NO: 1 or an amino acid sequence with at least 80%, such as at least 85%, such as at least 90%, such as at least 95%, or such as at least 99% identity to SEQ ID NO: 1.

In another embodiment of the disclosure, the enzyme with α-2,3-sialyltransferase activity is Neigon from *Neisseria gonorrhoeae* FA 1090 comprising or consisting of the amino acid sequence of SEQ ID NO: 2 or an amino acid sequence with at least 80%, such as at least 50%, such as at least 90%, such as at least 95%, or such as at least 99% identity to SEQ ID NO: 2.

In another embodiment of the disclosure, the enzyme with α-2,3-sialyltransferase activity is Poral from *Pasteurella oralis* comprising or consisting of the amino acid sequence of SEQ ID NO: 3 or an amino acid sequence with at least 80%, such as at least 85%, such as at least 90%, such as at least 95%, or such as at least 99% identity to SEQ ID NO: 3.

In another embodiment of the disclosure, the enzyme with α-2,3-sialyltransferase activity is PmN from *Pasteurella* comprising or consisting of the amino acid sequence of SEQ ID NO: 4 or an amino acid sequence with at least 80%, such as at least 85%, such as at least 90%, such as at least 95%, or such as at least 99% identity to SEQ ID NO: 4.

In an embodiment, the genetically modified cell expressing an α-2,3-sialyltransferase of the present disclosure results in a production of 3'SL which is at least equal to, at least 5%, such as at least 10%, such as at least 15% or such as at least 20% higher than the amount of 3'SL produced by a genetically modified cell expressing the α-2,3-sialyltransferase Nst (SEQ ID NO: 5), when the expression of Nst is regulated via a Plac promoter.

In an embodiment, the genetically modified cell expressing the α-2,3-sialyltransferase Clari1 comprising or consisting of the amino acid sequence of SEQ ID NO: 1 or an amino acid sequence with at least 80%, such as at least 85%, such as at least 90%, such as at least 95%, or such as at least 99% identity to SEQ ID NO: 1, results in a production of 3'SL which is at least equal to, at least 5%, such as at least 10%, such as at least 15% or such as at least 20 higher than the amount of 3'SL produced by a genetically modified cell expressing the α-2,3-sialyltransferase Nst (SEQ ID NO: 5), when the expression of Nst is regulated via a Plac promoter.

In an embodiment, the genetically modified cell expressing the α-2,3-sialyltransferase Neigon comprising or consisting of the amino acid sequence of SEQ ID NO: 2 or an amino acid sequence with at least 80%, such as at least 85%, such as at least 90%, such as at least 95%, or such as at least 99% identity to SEQ ID NO: 2, results in a production of 3'SL which is at least equal to, at least 5%, such as at least 7%, such as at least 10% or such as at least 15 higher than the amount of 3'SL produced by a genetically modified cell expressing the α-2,3-sialyltransferase Nst (SEQ ID NO: 5), when the expression of Nst is regulated via a Plac promoter.

In an embodiment, the genetically modified cell expressing the α-2,3-sialyltransferase Poral comprising or consisting of the amino acid sequence of SEQ ID NO: 3 or an amino acid sequence with at least 80%, such as at least 85%, such as at least 90%, such as at least 95%, or such as at least 99% identity to SEQ ID NO: 3, results in a production of 3'SL which is at least equal to, at least 2%, such as at least 4%, or such as at least 5% higher than the amount of 3'SL produced by a genetically modified cell expressing the α-2,3-sialyltransferase Nst (SEQ ID NO: 5), when the expression of Nst is regulated via a Plac promoter.

In an embodiment, the genetically modified cell expressing the α-2,3-sialyltransferase PmN comprising or consisting of the amino acid sequence of SEQ ID NO: 4 or an amino acid sequence with at least 80%, such as at least 80%, such as at least 90%, such as at least 95%, or such as at least 99% identity to SEQ ID NO: 4, results in a production of 3'SL which is at about equal to the amount of 3'SL produced by a genetically modified cell expressing the α-2,3-sialyltransferase Nst (SEQ ID NO: 5), when the expression of Nst is regulated via a Plac promoter.

In an embodiment, the genetically modified cell expressing an α-2,3-sialyltransferase of the present disclosure results in a production of 3'SL which is at least 5%, such as at least 10%, such as at least 15%, such as at least 20% or such as at least 25% higher than the amount of 3'SL produced by a genetically modified cell expressing the α-2,3-sialyltransferase PM70 (SEQ ID NO: 6), when the expression of PM70 is regulated via a Plac or PglpF promoter.

In an embodiment, the genetically modified cell expressing the α-2,3-sialyltransferase Clari1 comprising or consisting of the amino acid sequence of SEQ ID NO: 1 or an amino acid sequence with at least 80%, such as at least 85%, such as at least 90%, such as at least 95%, or such as at least 99% identity to SEQ ID NO: 1, results in a production of 3'SL which is at least 5%, such as at least 10%, such as at least 15%, such as at least 20% or such as at least 25% higher than the amount of 3'SL produced by a genetically modified cell expressing the α-2,3-sialyltransferase PM70 (SEQ ID NO: 6), when the expression of PM70 is regulated via a Plac or PglpF promoter.

In an embodiment, the genetically modified cell expressing the α-2,3-sialyltransferase Neigon comprising or consisting of the amino acid sequence of SEQ ID NO: 2 or an amino acid sequence with at least 80%, such as at least 85%, such as at least 90%, such as at least 95%, or such as at least 99% identity to SEQ ID NO: 2, results in a production of 3'SL which is at least 5%, such as at least 10%, such as at least 15%, such as at least 20% or such as at least 25% higher than the amount of 3'SL produced by a genetically modified cell expressing the α-2,3-sialyltransferase PM70 (SEQ ID NO: 6), when the expression of PM70 is regulated via a Plac or PglpF promoter.

In an embodiment, the genetically modified cell expressing the α-2,3-sialyltransferase Poral comprising or consisting of the amino acid sequence of SEQ ID NO: 3 or an amino acid sequence with at least 80%, such as at least 85%, such as at least 90%, such as at least 95%, or such as at least 99% identity to SEQ ID NO: 3, results in a production of 3'SL which is at least 3%, such as at least 5%, such as at least 7%, such as at least 9% or such as at least 10 higher than the amount of 3'SL produced by a genetically modified cell expressing the α-2,3-sialyltransferase PM70 (SEQ ID NO: 6), when the expression of PM70 is regulated via a Plac or PglpF promoter.

In an embodiment, the genetically modified cell expressing the α-2,3-sialyltransferase PmN comprising or consisting of the amino acid sequence of SEQ ID NO: 4 or an amino acid sequence with at least 80%, such as at least 85%, such as at least 90%, such as at least 95%, or such as at least 99% identity to SEQ ID NO: 4, results in a production of 3'SL which is at least 5%, such as at least 10%, such as at least 15%, such as at least 20% or such as at least 25% higher than the amount of 3'SL produced by a genetically modified cell expressing the α-2,3-sialyltransferase PM70 (SEQ ID NO: 6), when the expression of PM70 is regulated via a Plac or PglpF promoter.

In an embodiment, the genetically modified cell expressing an α-2,3-sialyltransferase of the present disclosure results in production of 3'SL while the genetically modified cell exhibits a stable growth over a wider range of growth rates compared to a genetically modified cell expressing the α-2,3-sialyltransferase Nst (SEQ ID NO: 5) when the expression of Nst is regulated by the PglpF promoter.

In an embodiment, the genetically modified cell expressing the α-2,3-sialyltransferase Clari1 comprising or consisting of the amino acid sequence of SEQ ID NO: 1 or an amino acid sequence with at least 80%, such as at least 85%, such as at least 90%, such as at least 95%, or such as at least 99% identity to SEQ ID NO: 1, results in production of 3'SL while the genetically modified cell exhibits stable growth over a wider range of growth rates compared to a genetically modified cell expressing the α-2,3-sialyltransferase Nst (SEQ ID NO: 5) when the expression of Nst is regulated via a PglpF promoter.

In an embodiment, the genetically modified cell expressing the α-2,3-sialyltransferase Poral comprising or consisting of the amino acid sequence of SEQ ID NO: 2 or an amino acid sequence with at least 80%, such as at least 85%, such as at least 90%, such as at least 95%, or such as at least 99% identity to SEQ ID NO: 2, results in production of 3'SL while the genetically modified cell exhibits stable growth over a wider range of growth rates compared to a genetically modified cell expressing the α-2,3-sialyltransferase Nst (SEQ ID NO: 5) when the expression of Nst is regulated via a PglpF promoter.

In an embodiment, the genetically modified cell expressing the α-2,3-sialyltransferase Neigon comprising or consisting of the amino acid sequence of SEQ ID NO: 3 or an amino acid sequence with at least 80%, such as at least 85%, such as at least 90%, such as at least 95%, or such as at least 99% identity to SEQ ID NO: 3, results in production of 3'SL while the genetically modified cell exhibits stable growth over a wider range of growth rates compared to a genetically modified cell expressing the α-2,3-sialyltransferase Nst (SEQ ID NO: 5) when the expression of Nst is regulated via a PglpF promoter.

In an embodiment, the genetically modified cell expressing the α-2,3-sialyltransferase PmN comprising or consisting of the amino acid sequence of SEQ ID NO: 4 or an amino acid sequence with at least 80%, such as at least 85%, such as at least 90%, such as at least 95%, or such as at least 99% identity to SEQ ID NO: 4, results in production of 3'SL while the genetically modified cell exhibits stable growth over a wider range of growth rates compared to a genetically modified cell expressing the α-2,3-sialyltransferase Nst (SEQ ID NO: 5) when the expression of Nst is regulated via a PglpF promoter.

Glycosyl-Donor-Nucleotide-Activated Sugar Pathways

When carrying out the method of this disclosure, preferably a glycosyltransferase mediated glycosylation reaction takes place in which an activated sugar nucleotide serves as glycosyl-donor. An activated sugar nucleotide generally has a phosphorylated glycosyl residue attached to a nucleoside. A specific glycosyl transferase enzyme accepts only a specific sugar nucleotide. Thus, preferably the following activated sugar nucleotides are involved in the glycosyl transfer: glucose-UDP-GlcNAc, UDP-galactose, UDP-glucose, UDP-N-acetylglucosamine, UDP-N-acetylgalactosamine (GlcNAc) and CMP-N-acetylneuraminic acid. The genetically modified cell according to the present disclosure can comprise one or more pathways to produce a nucleotide-activated sugar selected from the group consisting of glucose-UDP-GlcNAc, GDP-fucose, UDP-galactose, UDP-glucose, UDP-N-acetylglucosamine, UDP-N-acetylgalactosamine and CMP-N-acetylneuraminic acid.

In one embodiment of the method, the genetically modified cell is capable of producing one or more activated sugar nucleotides mentioned above by a de novo pathway. In this regard, an activated sugar nucleotide is made by the cell under the action of enzymes involved in the de novo biosynthetic pathway of that respective sugar nucleotide in a stepwise reaction sequence starting from a simple carbon source like glycerol, sucrose, fructose or glucose (for a review for monosaccharide metabolism see e.g. H. H. Freeze and A. D. Elbein: Chapter 4: Glycosylation precursors, in: Essentials of Glycobiology, 2nd edition (Eds. A. Varki et al.), Cold Spring Harbour Laboratory Press (2009)).

The enzymes involved in the de novo biosynthetic pathway of an activated sugar nucleotide can be naturally present in the cell or introduced into the cell by means of gene technology or recombinant DNA techniques, all of them are parts of the general knowledge of the skilled person.

In another embodiment, the genetically modified cell can utilize salvaged monosaccharides for sugar nucleotide. In the salvage pathway, monosaccharides derived from degraded oligosaccharides are phosphorylated by kinases, and converted to nucleotide sugars by pyrophosphorylases. The enzymes involved in the procedure can be heterologous ones, or native ones of the host cell.

Sialic acid sugar nucleotide synthesis pathway Preferably, the genetically modified cell according to the present disclosure comprises a sialic acid sugar nucleotide synthesis capability, i.e., the genetically modified cell comprises a biosynthetic pathway for making a sialate sugar nucleotide, such as CMP-N-acetylneuraminic acid as glycosyl-donor for the alpha-2,3-sialyltransferase of the present disclosure. E.g., the genetically modified cell comprises a sialic acid synthetic capability through provision of an exogenous UDP-GlcNAc 2-epimerase (e.g., NeuC of *Campylobacter jejuni* (GenBank AAK91727.1) or equivalent (e.g., (GenBank CAR04561.1), a Neu5Ac synthase (e.g., NeuB of *C. jejuni* (GenBank AAK91726.1) or equivalent, (e.g., *Flavobacterium limnosediminis* sialic acid synthase, GenBank WP_023580510.1), and/or a CMP-Neu5Ac synthetase (e.g., NeuA of *C. jejuni* (GenBank AAK91728.1) or equivalent, (e.g., *Vibrio brasiliensis* CMP-sialic acid synthase, GenBank WP_006881452.1).

In one or more examples UDP-GlcNAc 2-epimerase, CMP-Neu5Ac synthetase, Neu5Ac synthase from *Campylobacter jejuni*, also referred to as NeuBCA from *Campylobacter jejuni* or simply the neuBCA operon, may be plasmid borne or integrated into the genome of the genetically modified cell. Preferably, the sialic acid sugar nucleotide pathway is encoded by the nucleic acid sequence encoding NeuBCA from *Campylobacter jejuni* (SEQ ID NO: 35) or a functional variant thereof having an amino acid sequence which is at least 80% identical, such as at least 85%, such as at least 90% or such as at least 99% to SEQ ID NO: 35.

Additionally, the nucleic acid sequence encoding NeuBCA is preferably encoded from a high-copy plasmid bearing the neuBCA operon. In embodiments, the high-copy plasmid is the BlueScribe M13 plasmid (pBS). In relation to the present disclosure, a high-copy plasmid is a plasmid that that replicates to a copy number above 50 when introduced into the cell.

A Deficient Sialic Acid Catabolic Pathway

The genetically modified cell of the present disclosure preferably has a deficient sialic acid catabolic pathway. By "sialic acid catabolic pathway" is meant a sequence of reactions, usually controlled, and catalysed by enzymes, which results in the degradation of sialic acid. An exemplary sialic acid catabolic pathway described hereafter is the *E. coli* pathway. In this pathway, sialic acid (Neu5Ac; N-acetylneuraminic acid) is degraded by the enzymes NanA (N-acetylneuraminic acid lyase) and NanK (N-acetylmannosamine kinase) and NanE (N-acetylmannosamine-6-phosphate epimerase), all encoded from the nanATEK-yhcH operon, and repressed by NanR (http://ecocyc.org/ECOLI). A deficient sialic acid catabolic pathway is rendered in the *E. coli* host by introducing a mutation in the endogenous nanA (N-acetylneuraminate lyase) (e.g., GenBank Accession Number D00067.1 (GL216588)) and/or nanK (N-acetylmannosamine kinase) genes (e.g., GenBank Accession Number (amino acid) BAE77265.1 (GL85676015)), and/or nanE (N-acetylmannosamine-6-phosphate epimerase, GI: 947745), incorporated herein by reference). Optionally, the nanT (N-acetylneuraminate transporter) gene is also inactivated or mutated. Other intermediates of sialic acid metabolism include: (ManNAc-6-P) N-acetylmannosamine-6-phosphate; (GlcNAc-6-P) N-acetylglucosamine-6-phosphate; (GlcN-6-P) Glucosamine-6-phosphate, and (Fruc-6-P) Fructose-6-phosphate. In some preferred embodiments, nanA is mutated. In other preferred embodiments, nanA and nanK are mutated, while nanE remains functional. In another preferred embodiment, nanA and nanE are mutated, while nanK has not been mutated, inactivated or deleted. A mutation is one or more changes in the nucleic acid sequence coding the gene product of nanA, nanK, nanE, and/or nanT. E.g., the mutation may be 1, 2, up to 5, up to 10, up to 25, up to 50 or up to 100 changes in the nucleic acid sequence. E.g., the nanA, nanK, nanE, and/or nanT genes are mutated by a null mutation. Null mutations as described herein encompass amino acid substitutions, additions, deletions, or insertions, which either cause a loss of function of the enzyme (i.e., reduced or no activity) or loss of the enzyme (i.e., no gene product). By "deleted" is meant that the coding region is removed completely or in part such that no (functional) gene product is produced. By inactivated is meant that the coding sequence has been altered such that the resulting gene product is functionally inactive or encodes for a gene product with less than 100%, e.g., 90%, 80%, 70%, 60%, 50%, 40%, 30% or 20% of the activity of the native, naturally occurring, endogenous gene product. Thus, in the present disclosure, nanA, nanK, nanE, and/or nanT genes are preferably inactivated.

Major Facilitator Superfamily (MFS) Transporter Proteins

The oligosaccharide product, the HMO produced by the cell, can be accumulated both in the intra- and the extracellular matrix. The product can be transported to the supernatant in a passive way, i.e., it diffuses outside across the cell membrane. Alternatively, the HMO transport can be facilitated by major facilitator superfamily transporter proteins that promote the effluence of sugar derivatives from the cell to the supernatant. The major facilitator superfamily transporter can be present exogenously or endogenously and is overexpressed under the conditions of the fermentation to enhance the export of the oligosaccharide derivative (HMO) produced. The specificity towards the sugar moiety of the product to be secreted can be altered by mutation by means of known recombinant DNA techniques.

Thus, the genetically modified cell according to the present disclosure can further comprise a nucleic acid sequence encoding a major facilitator superfamily transporter protein capable of exporting the sialylated human milk oligosaccharide product or products.

In the resent years, several new and efficient major facilitator superfamily transporter proteins have been identified, each having specificity for different recombinantly produced HMOs and development of recombinant cells expressing said proteins are advantageous for high scale industrial HMO manufacturing. WO2021/123113 claim different *E. coli* and heterologous transporters for the export of 3'SL, 6'SL and LST-a.

Thus, in one or more exemplary embodiments, the genetically engineered cell according to the method described herein further comprises a gene product that acts as a major facilitator superfamily transporter. The gene product that acts as a major facilitator superfamily transporter may be encoded by a recombinant nucleic acid sequence that is expressed in the genetically engineered cell. The recombinant nucleic acid sequence encoding a major facilitator superfamily transporter, may be integrated into the genome of the genetically engineered cell, or expressed using a plasmid.

In one embodiment, the genetically modified cell of the disclosure comprises a nucleic acid sequence encoding a major facilitator superfamily transporter protein capable of exporting the sialylated human milk oligosaccharide product into the extracellular medium, in particular, the transporters with specificity towards 3'SL is preferred.

Nec

In an embodiment, the genetically modified cell of the disclosure comprises a nucleic acid sequence encoding an efflux transporter protein capable of exporting the sialylated human milk oligosaccharide product, such as 3'SL; into the extracellular medium. In the current context, said efflux transporter protein is preferably a heterologous gene encoding a putative MFS (major facilitator superfamily) transporter protein, originating from the bacterium *Rosenbergiella nectarea*. More specifically, the disclosure relates to a genetically modified cell optimized to produce an oligosaccharide, in particular a sialylated HMO, comprising a recombinant nucleic acid encoding a protein having at least 80%, such as at least 85%, such as at least 90% such as at least 95% or 100% sequence identity to the amino acid sequence of the amino acid sequence having GenBank accession ID WP_092672081.1 or SEQ ID NO: 38.

Additionally, the MFS transporter protein with the GenBank accession ID WP_092672081.1 is further described in WO2021/148615 and is identified herein as "Nec protein" or "Nec transporter" or "Nec", interchangeably; a nucleic acid sequence encoding Nec protein is identified herein as "nec coding nucleic acid/DNA" or "nec gene" or "nec".

Nec is expected to facilitate an increase in the efflux of the produced sialylated HMOs, e.g., 3'SL in the genetically engineered cells of the current disclosure.

Accordingly, in an embodiment, the genetically modified cell of the present disclosure comprises a nucleic acid sequence encoding the Nec transporter protein.

Fred/YberC

In embodiments, the genetically modified cell of the present disclosure comprises a nucleic acid sequence encoding an efflux transporter protein capable of exporting the simple sialylated human milk oligosaccharide product such as 3'SL and 6'SL into the extracellular medium. In the current context, said efflux transporter protein is preferably a heterologous gene encoding a putative MFS (major facilitator superfamily) transporter protein, originating from the bacterium *Yersinia frederiksenii* and/or the bacterium *Yersinia bercovieri*. More specifically, the disclosure relates to a genetically modified cell optimized to produce an oligosaccharide, in particular a sialylated HMO, comprising a recombinant nucleic acid encoding a protein having at least 80%, such as at least 85%, such as at least 90% such as at least 95% or 100% sequence identity to the amino acid sequence of the amino acid sequence having the GenBank accession ID WP_087817556.1 (SEQ ID NO: 40) or GenBank accession EEQ08298 (SEQ ID NO: 39).

The MFS transporter protein with the GenBank accession ID WP_087817556.1 is further described in WO2021/148620 and is identified herein as "Fred protein" or "Fred transporter" or "Fred", interchangeably; a nucleic acid sequence encoding Fred protein is identified herein as "fred coding nucleic acid/DNA" or "fred gene" or "fred".

Accordingly, in an embodiment, the genetically modified cell of the present disclosure comprises a nucleic acid sequence encoding the Nec or Fred transporter protein.

Additionally, the MFS transporter protein with the GenBank accession ID EEQ08298 is further described in WO2021/148610 and is identified herein as "YberC protein" or "YberC transporter" or "YberC", interchangeably; a nucleic acid sequence encoding YberC protein is identified herein as "YberC coding nucleic acid/DNA" or "yberC gene" or "yberC".

Fred and YberC facilitate an increase in the efflux of the produced sialylated HMOs, e.g., 3'SL in the genetically engineered cells of the current disclosure.

Accordingly, in an embodiment, the genetically modified cell of the present disclosure comprises a nucleic acid sequence encoding the Fred transporter protein. In an embodiment, the genetically modified cell of the present disclosure comprises a nucleic acid sequence encoding the YberC transporter protein.

The Genetically Modified Cell

In the present context, the terms "a genetically modified cell" and "a genetically engineered cell" are used interchangeably. As used herein "a genetically modified cell" is a host cell whose genetic material has been altered by human intervention using a genetic engineering technique, such a technique is e.g., but not limited to transformation or transfection e.g., with a heterologous polynucleotide sequence, Crisper/Cas editing and/or random mutagenesis. In one embodiment the genetically engineered cell has been transformed or transfected with a recombinant nucleic acid sequence.

The genetic modifications can e.g., be selected from inclusion of glycosyltransferases, and/or metabolic pathway engineering and inclusion of MFS transporters as described in the above sections, which the skilled person will know how to combine into a genetically modified cell capable of producing one or more sialylated HMO's.

In one aspect of the disclosure, the genetically modified cell comprises a recombinant nucleic acid sequence encoding an enzyme with α-2,3-sialyltransferase activity, which is capable of producing at least 5% more 3'SL molar HMO content compared to a cell expressing the α-2,3-sialyltransferase Nst wherein the expression of Nst is regulated by a Plac promoter.

The genetically engineered cell is preferably a microbial cell, such as a prokaryotic cell or eukaryotic cell. Appropriate microbial cells that may function as a host cell include bacterial cells, archaebacterial cells, algae cells and fungal cells.

The genetically engineered cell may be e.g., a bacterial or yeast cell. In one preferred embodiment, the genetically engineered cell is a bacterial cell.

Host cells Regarding the bacterial host cells, there are, in principle, no limitations; they may be eubacteria (gram-positive or gram-negative) or archaebacteria, as long as they allow genetic manipulation for insertion of a gene of interest and can be cultivated on a manufacturing scale. Preferably, the host cell has the property to allow cultivation to high cell densities. Non-limiting examples of bacterial host cells that are suitable for recombinant industrial production of an HMO(s) according to the disclosure could be *Erwinia herbicola* (*Pantoea agglomerans*), *Citrobacter freundii*, *Campylobacter* sp, *Pantoea citrea*, *Pectobacterium carotovorum*, or *Xanthomonas campestris*. Bacteria of the genus *Bacillus* may also be used, including *Bacillus subtilis*, *Bacillus licheniformis*, *Bacillus coagulans*, *Bacillus thermophilus*, *Bacillus laterosporus*, *Bacillus megaterium*, *Bacillus mycoides*, *Bacillus pumilus*, *Bacillus lentus*, *Bacillus cereus*, and *Bacillus circulans*. Similarly, bacteria of the genera *Lactobacillus* and *Lactococcus* may be engineered using the methods of this disclosure, including but not limited to *Lactobacillus acidophilus*, *Lactobacillus salivarius*, *Lactobacillus plantarum*, *Lactobacillus helveticus*, *Lactobacillus delbrueckii*, *Lactobacillus rhamnosus*, *Lactobacillus bulgaricus*, *Lactobacillus crispatus*, *Lactobacillus gasseri*, *Lactobacillus casei*, *Lactobacillus reuteri*, *Lactobacillus jensenii*, and *Lactococcus lactis*. *Streptococcus thermophiles* and *Proprionibacterium freudenreichii* are also suitable bacterial species for the disclosure described herein. Also included as part of this disclosure are strains, engineered as described here, from the genera *Enterococcus* (e.g., *Enterococcus faecium* and *Enterococcus thermophiles*), *Bifidobacterium* (e.g., *Bifidobacterium longum*, *Bifidobacterium infantis*, and *Bifidobacterium bifidum*), *Sporolactobacillus* spp., *Micromomospora* spp., *Micrococcus* spp., *Rhodococcus* spp., and *Pseudomonas* (e.g., *Pseudomonas fluorescens* and *Pseudomonas aeruginosa*).

Non-limiting examples of fungal host cells that are suitable for recombinant industrial production of a heterologous product are e.g., yeast cells, such as *Komagataella phaffii*, *Kluyveromyces lactis*, *Yarrowia lipolytica*, *Pichia pastoris*, and *Saccharomyces cerevisiae* or filamentous fungi such as *Aspargillus* sp, *Fusarium* sp or *Thricoderma* sp, exemplary species are *A. niger*, *A. nidulans*, *A. oryzae*, *F. solani*, *F. graminearum* and *T. reesei*.

In one or more exemplary embodiments, the genetically engineered cell is selected from the group consisting of *Escherichia* sp., *Bacillus* sp., *lactobacillus* sp., *Corynebacterium* sp. and *Campylobacter* sp.

In one or more exemplary embodiments, the genetically engineered cell is selected from the group consisting of *Escherichia coli*, *Bacillus subtilis*, *lactobacillus lactis*, *Corynebacterium glutamicum*, *Yarrowia lipolytica*, *Pichia pastoris*, and *Saccharomyces cerevisiae*.

In one or more exemplary embodiments, the genetically engineered cell is *B. subtilis*.

In one or more exemplary embodiments, the genetically engineered cell is *S. Cerevisiae* or *P. pastoris*.

In one or more exemplary embodiments, the genetically engineered cell is *Escherichia coli*.

In one or more exemplary embodiments, the disclosure relates to a genetically engineered cell, wherein the cell is derived from the *E. coli* K-12 strain or DE3.

A Recombinant Nucleic Acid Sequence

The present disclosure relates to a genetically modified cell comprising a recombinant nucleic acid sequence encoding an enzyme with α-2,3-sialyltransferase activity, such as an enzyme selected from the group consisting of Clari1, Neigon, Poral and PmN, wherein said cell produces Human Milk Oligosaccharides (HMO), in particular a sialylated HMO, and preferably 3'SL.

In the present context, the term "recombinant nucleic acid sequence", "recombinant gene/nucleic acid/nucleotide sequence/DNA encoding" or "coding nucleic acid sequence" is used interchangeably and intended to mean an artificial nucleic acid sequence (i.e. produced in vitro using standard laboratory methods for making nucleic acid sequences) that comprises a set of consecutive, non-overlapping triplets (codons) which is transcribed into mRNA and translated into a protein when under the control of the appropriate control sequences, i.e., a promoter sequence.

The boundaries of the coding sequence are generally determined by a ribosome binding site located just upstream of the open reading frame at the 5'end of the mRNA, a transcriptional start codon (AUG, GUG or UUG), and a translational stop codon (UAA, UGA or UAG). A coding sequence can include, but is not limited to, genomic DNA, cDNA, synthetic, and recombinant nucleic acid sequences.

The term "nucleic acid" includes RNA, DNA and cDNA molecules. It is understood that, as a result of the degeneracy of the genetic code, a multitude of nucleic acid sequences encoding a given protein may be produced.

The recombinant nucleic acid sequence may be a coding DNA sequence e.g., a gene, or non-coding DNA sequence e.g., a regulatory DNA, such as a promoter sequence or other non-coding regulatory sequences.

The recombinant nucleic acid sequence may in addition be heterologous. As used herein "heterologous" refers to a polypeptide, amino acid sequence, nucleic acid sequence or nucleotide sequence that is foreign to a cell or organism, i.e., to a polypeptide, amino acid sequence, nucleic acid molecule or nucleotide sequence that does not naturally occurs in said cell or organism.

The disclosure also relates to a nucleic acid construct comprising a coding nucleic sequence, i.e. recombinant DNA sequence of a gene of interest, e.g., a sialyltransferase gene, and a non-coding regulatory DNA sequence, e.g., a promoter DNA sequence, e.g., a recombinant promoter sequence derived from the promoter sequence of the lac operon or the glp operon, or a promoter sequence derived from another genomic promoter DNA sequence, or a synthetic promoter sequence, wherein the coding and promoter sequences are operably linked.

The term "operably linked" refers to a functional relationship between two or more nucleic acid (e.g., DNA) segments. It refers to the functional relationship of a transcriptional regulatory sequence to a transcribed sequence. E.g., a promoter sequence is operably linked to a coding sequence if it stimulates or modulates the transcription of the coding sequence in an appropriate host cell or other expression system.

Generally, promoter sequences that are operably linked to a transcribed sequence are physically contiguous to the transcribed sequence, i.e., they are cis-acting.

In one exemplified embodiment, the nucleic acid construct of the disclosure may be a part of the vector DNA, in another embodiment, the construct it is an expression cassette/cartridge that is integrated in the genome of a host cell.

Accordingly, the term "nucleic acid construct" means an artificially constructed segment of nucleic acids, in particular a DNA segment, which is intended to be inserted into a target cell, e.g., a bacterial cell, to modify expression of a gene of the genome or expression of a gene/coding DNA sequence which may be included in the construct. Thus, in embodiments, the present disclosure relates to a nucleic acid construct comprising a recombinant nucleic acid sequence encoding a sialyltransferase, wherein said recombinant nucleic acid sequence is selected from the group consisting of nucleic acid sequences encoding Clari1, Neigon, Poral, and PmN, such as SEQ ID NO: 23, 24, 25 or 27, or functional variants thereof.

One embodiment of the disclosure is a nucleic acid construct comprising a recombinant nucleic acid sequence encoding a sialyltransferase, wherein said recombinant nucleic acid sequence is selected from the group consisting of a) Clari1 comprising or consisting of the nucleic acid sequences of SEQ ID NO: 23 or an nucleic acid sequence with at least 80%, such as at least 85%, such as at least 90%, such as at least 95%, or such as at least 99% identity to SEQ ID NO: 23; b) Neigon comprising or consisting the nucleic acid sequences of SEQ ID NO: 24 or an nucleic acid sequence with at least 80%, such as at least 84%, such as at least 90%, such as at least 95%, or such as at least 99% identity to SEQ ID NO: 24; c) Poral comprising or consisting the nucleic acid sequence of SEQ ID NO: 25 or an nucleic acid sequence with at least 80%, such as at least 85%, such as at least 90%, such as at least 95%, or such as at least 99% identity to SEQ ID NO: 25 and d) PmN comprising or consisting the nucleic acid sequence of SEQ ID NO: 27 or an nucleic acid sequence with at least 80%, such as at least 85%, such as at least 90%, such as at least 95%, or such as at least 99% identity to SEQ ID NO: 27. Preferably, the sialyltransferase encoding sequence is under the control of a promoter sequence selected from promotor sequences with a nucleic acid sequence as identified in Table 2.

TABLE 2

Selected promoter sequences

| Promoter name | % Activity relative to PglpF* | Strength | Reference | Seq ID in appl. |
|---|---|---|---|---|
| PmglB_70UTR_SD8 | 291% | high | WO2020255054 | 22 |
| PmglB_70UTR_SD10 | 233-281% | high | WO2020255054 | 42 |
| PmglB_54UTR | 197% | high | WO2020255054 | 19 |
| Plac_70UTR | 182-220% | high | WO2019123324 | 18 |
| PmglB_70UTR_SD9 | 180-226% | high | WO2020255054 | 41 |
| PmglB_70UTR_SD4 | 153%-353% | high | WO2020255054 | 21 |
| PmglB_70UTR_SD5 | 146-152% | high | WO2020255054 | 43 |
| PglpF_16UTR_SD4 | 140-161% | high | WO2019123324 | 44 |
| PmglB_70UTR_SD7 | 127-173% | high | WO2019123324 | 45 |
| PmglB_70UTR | 124-234% | high | WO2020255054 | 20 |
| PglpA_70UTR | 102-179% | high | WO2019123324 | 46 |
| PglpT_70UTR | 102-240% | high | WO2019123324 | 47 |
| PglpF | 100% | high | WO2019123324 | 13 |
| PglpF_16UTR_SD10 | 88-96% | high | WO2019123324 | 48 |
| PglpF_16UTR_SD5 | 82-91% | high | WO2019123324 | 49 |

TABLE 2-continued

Selected promoter sequences

| Promoter name | % Activity relative to PglpF* | Strength | Reference | Seq ID in appl. |
|---|---|---|---|---|
| PglpF_16UTR_SD8 | 81-82% | high | WO2019123324 | 50 |
| PmglB_16UTR | 78-171% | high | WO2019123324 | 51 |
| PglpF_16UTR_SD9 | 73-93% | middle | WO2019123324 | 52 |
| PglpF_16UTR_SD7 | 47-57% | middle | WO2019123324 | 16 |
| PglpF_16UTR_SD6 | 46-47% | middle | WO2019123324 | 53 |
| PglpA_16UTR | 38-64% | middle | WO2019123324 | 54 |
| Plac_wt* | 15-28% | low | WO2019123324 | 17 |
| PglpF_16UTR_SD3 | 9% | low | WO2019123324 | 15 |
| PglpF_16UTR_SD1 | 5% | low | WO2019123324 | 14 |

*The promoter activity is assessed in the LacZ assay described below with the PglpF promoter run as positive reference in the same assay. To compare across assays the activity is calculated relative to the PglpF promoter, a range indicates results from multiple assays.

The promoter may be of heterologous origin, native to the genetically modified cell or it may be a recombinant promoter, combining heterologous and/or native elements.

One way to increase the production of a product may be to regulate the production of the desired enzyme activity used to produce the product, such as the glycosyltransferases or enzymes involved in the biosynthetic pathway of the glycosyl donor.

Increasing the promoter strength driving the expression of the desired enzyme may be one way of doing this. The strength of a promoter can be assessed using a lacZ enzyme assay where β-galactosidase activity is assayed as described previously (see e.g., Miller J. H. Experiments in molecular genetics, Cold spring Harbor Laboratory Press, N Y, 1972). Briefly the cells are diluted in Z-buffer and permeabilized with sodium dodecyl sulfate (0.1%) and chloroform. The LacZ assays is performed at 30° C. Samples are preheated, the assay initiated by addition of 200 μl ortho-nitro-phenyl-β-galactosidase (4 mg/ml) and stopped by addition of 500 μl of 1 M $Na_2CO_3$ when the sample had turned slightly yellow. The release of ortho-nitrophenol is subsequently determined as the change in optical density at 420 nm. The specific activities are reported in Miller Units (MU) [A420/(min*ml*A600)]. A regulatory element with an activity above 10,000 MU is considered strong and a regulatory element with an activity below 3,000 MU is considered weak, what is in between has intermediate strength. An example of a strong regulatory element is the PglpF promoter with an activity of approximately 14.000 MU and an example of a weak promoter is Plac which when induced with IPTG has an activity of approximately 2300 MU.

Not all enzymes are equally well tolerated by the host cell when expressed high amounts as is the case with the alpha-2,3-sialyltransferase, Nst, as shown in Example 1 and 2. Therefore, when Nst is used for the production of 3'SL it is under control of the weak promoter Plac, since when it is under control of PglpF the growth of the host cell is affected.

In one aspect of the disclosure, the expression of the recombinant nucleic acid sequence encoding an enzyme with α-2,3-sialyltransferase activity, is regulated by a promoter which confers an enhanced expression of said enzyme with α-2,3-sialyltransferase, selected from the group of promoters consisting of Plac, PglpF, PglpA, PglpT or PmglB and variants thereof. Preferably, the sialyltransferase is under the control of a strong recombinant promoter selected from the group consisting of SEQ ID NOs 13, 18, 19, 20, 21, 22, 41, 42, 43, 44, 45, 46, 47, 48, 49, 50 and 51.

In another aspect of the disclosure, the expression of the recombinant nucleic acid sequence encoding an enzyme with α-2,3-sialyltransferase activity, is regulated by a recombinant promoter which confers an enhanced expression of said enzyme with α-2,3-sialyltransferase activity.

Additionally, constructs of the present disclosure may in addition comprise one or more nucleic acid sequences encoding a β-1,3-N-acetyl-glucosaminyl-transferase such as a nucleic acid sequence of SEQ ID NO 36: encoding LgtA, a β-1,3-galactosyltransferase such as a nucleic acid sequence of SEQ ID NO: 37 encoding GalTK, one or more MFS transporter such as a nucleic acid sequence of SEQ ID NO: 38, 39 or 40 encoding Nec, YberC or Fred and one or more nucleic acid sequences encoding one or more sialic acid sugar nucleotide synthesis pathway enzymes such as a nucleic acid sequences of SEQ ID NO: 35 encoding the sialic acid sugar nucleotide synthesis pathway enzymes. In embodiments the expression of said nucleic acid sequences of the present disclosure is under control of a PglpF (SEQ ID NO: 13) or Plac_70 UTR (SEQ ID NO: 18) promoter or PmglB_70 UTR (SEQ ID NO: 20) or variants thereof such as promoters identified in Table 2, in particular promoters selected from the group consisting of SEQ ID NOs 13, 18, 19, 20, 21, 22, 41, 42, 43, 44, 45, 46, 47, 48, 49, 50 and 51.

Further suitable variants of PglpF and PmglB promoter sequences are described in or WO2019/123324 and WO2020/255054 respectively (hereby incorporated by reference).

Integration of the nucleic acid construct of interest comprised in the construct (expression cassette) into the bacterial genome can be achieved by conventional methods, e.g. by using linear cartridges that contain flanking sequences homologous to a specific site on the chromosome, as described for the attTn7-site (Waddell C. S. and Craig N. L., Genes Dev. (1988) February; 2(2):137-49); methods for genomic integration of nucleic acid sequences in which recombination is mediated by the Red recombinase function of the phage λ or the RecE/RecT recombinase function of the Rac prophage (Murphy, J Bacteriol. (1998); 180(8): 2063-7; Zhang et al., Nature Genetics (1998) 20: 123-128 Muyrers et al., EMBO Rep. (2000) 1(3): 239-243); methods based on Red/ET recombination (Wenzel et al., Chem Biol. (2005), 12(3):349-56; Vetcher et al., Appl Environ Microbiol. (2005); 71(4):1829-35; or positive clones, i.e., clones that carry the expression cassette, can be selected e.g., by means of a marker gene, or loss or gain of gene function.

In one or more exemplary embodiments, the present disclosure relates to one or more recombinant nucleic acid sequences as illustrated in SEQ ID NOs: 23, 24, 25 or 27.

In particular, the present disclosure relates to one or more of a recombinant nucleic acid sequence and/or to a functional homologue thereof having a sequence which is at least 70% identical to SEQ ID NOs: 23, 24, 25 or 27, such as at least 75% identical, at least 80 identical, at least 85% identical, at least 90% identical, at least, at least 95% identical, at least 98% identical, or 100% identical.

Sequence Identity

The term "sequence identity" as used herein describes the relatedness between two amino acid sequences or between two nucleotide sequences, i.e., a candidate sequence (e.g., a sequence of the disclosure) and a reference sequence (such as a prior art sequence) based on their pairwise alignment. For purposes of the present disclosure, the sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later (available at https://www.ebi.ac.uk/Tools/psa/emboss needle/). The parameters used are gap open penalty of 10, gap extension penalty of 0.5, and the EBLOSUM62 (EMBOSS version of 30 BLOSUM62) substitution matrix. The output of Needle labeled "longest identity" (obtained using the -nobrief option) is used as the percent identity and is calculated as follows: (Identical Residues×100)/(Length of Alignment−Total Number of Gaps in Alignment).

For purposes of the present disclosure, the sequence identity between two nucleotide sequences is determined using the Needleman-Wunsch algorithm (Needleman and Wunsch, 1 970, supra) as implemented in the Needle program of the EMBOSS package (EMBOSS: The European Molecular Biology Open Software Suite, Rice et al., 2000, Trends Genet. 16: 276-277), 10 preferably version 5.0.0 or later. The parameters used are gap open penalty of 10, gap extension penalty of 0.5, and the DNAFULL (EMBOSS version of NCBI NUC4.4) substitution matrix. The output of Needle labeled "longest identity" (obtained using the -nobrief option) is used as the percent identity and is calculated as follows: (Identical Deoxyribonucleotides×100)/(Length of Alignment—Total Number of Gaps in Alignment).

Functional Homologue

A functional homologue or functional variant of a protein/nucleic acid sequence as described herein is a protein/nucleic acid sequence with alterations in the genetic code, which retain its original functionality. A functional homologue may be obtained by mutagenesis or may be natural occurring variants from the same or other species. The functional homologue should have a remaining functionality of at least 50%, such as at least 60%, 70%, 80%, 90% or 100% compared to the functionality of the protein/nucleic acid sequence.

A functional homologue of any one of the disclosed amino acid or nucleic acid sequences can also have a higher functionality. A functional homologue of any one of the amino acid sequences shown in table 1 or a recombinant nucleic acid encoding any one of the sequences of table 4, should ideally be able to participate in the production of sialylated HMOs, in terms of increased HMO yield, export of HMO product out of the cell or import of substrate for the HMO production, such as lactose, improved purity/by-product formation, reduction in biomass formation, viability of the genetically engineered cell, robustness of the genetically engineered cell according to the disclosure, or reduction in consumables needed for the production.

Use of a Genetically Modified Cell

The disclosure also relates to any commercial use of the genetically modified cell(s) or the nucleic acid construct(s) disclosed herein, such as, but not limited to, in a method for producing a sialylated human milk oligosaccharide (HMO).

In an exemplified embodiment, the genetically modified cell and/or the nucleic acid construct according to the disclosure is used in the manufacturing of HMOs.

In an exemplified embodiment, the genetically modified cell and/or the nucleic acid construct according to the disclosure is used in the manufacturing of one or more sialylated HMO(s), wherein the sialylated HMOs are 3'SL, FSL, DSLNT and LST-a.

Production of these HMO's may require the presence of two or more glycosyltransferase activities.

In one or more embodiments, the genetically engineered cell and/or the nucleic acid construct is used in the manufacturing of 3'SL. Preferably, 3'SL is the only HMO manufactured.

A Method for Producing Sialylated Human Milk Oligosaccharides (HMOs)

The present disclosure also relates to a method for producing a sialylated human milk oligosaccharide (HMO), said method comprises culturing a genetically modified cell according to the present disclosure. Example 1 of the present disclosure has identified the heterologous alpha-2,3-sialyltransferases Clari1, Neigon, Poral and PmN (SEQ ID NO: 1, 2, 3 and 4, respectively), that when expressed in a production strain produces 3'SL and exhibit stable growth when compared to the Nst alpha-2,3-sialyltransferases.

The present disclosure relates to a method for producing human milk oligosaccharides (HMOs), and in particular 3'SL is produced. In particular 3'SL without the presence of other HMOs.

The present disclosure also relates to a method for producing human milk oligosaccharides (HMOs) wherein the amount of 3'SL produced is at least 5%, such as at least 10%, such as at least 15% or such as at least 20% higher than the amount of 3'SL produced by a method comprising the use of a genetically modified cell expressing the α-2,3-sialyltransferase Nst (SEQ ID NO: 5), when the expression of Nst is regulated via a Plac promoter.

The present disclosure also relates to a method for producing human milk oligosaccharides (HMOs) wherein the amount of 3'SL is at least 5%, such as at least 10%, such as at least 15%, such as at least 20% or such as at least 25% higher than the amount of 3'SL produced by a method comprising the use of a genetically modified cell expressing the α-2,3-sialyltransferase PM70, when the expression of PM70 is regulated via a Plac or PglpF promoter.

The present disclosure thus relates to a method for producing a sialylated human milk oligosaccharide (HMO), said method comprising culturing a genetically modified cell comprising a recombinant nucleic acid sequence encoding an enzyme with α-2,3-sialyltransferase activity, wherein said enzyme is selected from the group consisting of:

a. Clari1 comprising or consisting of the amino acid sequence of SEQ ID NO: 1 or an amino acid sequence with at least 80%, such as at least 85%, such as at least 90%, such as at least 95%, or such as at least 99% identity to SEQ ID NO: 1, b. Neigon comprising or consisting of the amino acid sequence of SEQ ID NO: 2 or an amino acid sequence with at least 80%, such as at least 85%, such as at least 90%, such as at least 95%, or such as at least 99% identity to SEQ ID NO: 2, c. Poral comprising or consisting of the amino acid sequence of SEQ ID NO: 3 or an amino acid sequence with at least 80%, such as at least 85%, such as at least 90%, such as at least 95%, or such as at least 99% identity to SEQ ID NO: 3 and d. PmN comprising or consisting of the amino acid sequence of SEQ ID NO: 4 or an amino acid sequence with at least 80%, such as at least 85%, such as at least 90%, such as at least 95%, or such as at least 99% identity to SEQ ID NO: 4.

In further embodiments the genetically modified cell comprises at least one additional modification according to the present disclosure.

In one or more exemplary embodiments, the α-2,3-sialyltransferase of the present disclosure is under control of a PglpF, a PglpA_70 UTR, PglpT_70 UTR, a Plac_70 UTR, or a Pmg16_70 UTR promoter or variants thereof as disclosed in table 2. Preferably, the sialyltransferase is under the control of a recombinant promoter selected from the group consisting of SEQ ID NOs 13, 18, 19, 20, 21, 22, 41, 42, 43, 44, 45, 46, 47, 48, 49, 50 and 51. Thus, in an exemplary embodiment, the α-2,3-sialyltransferase of the present disclosure is under control of a PglpF promoter or a variant thereof as disclosed in table 2. In another exemplary embodiment, the α-2,3-sialyltransferase of the present disclosure is under control of a Pmg16_70 UTR promoter or a variant thereof as disclosed in table 2.

Further genetic modifications can e.g., be selected from inclusion of additional glycosyltransferases and/or metabolic pathway engineering, and inclusion of MFS transporters, as described in the above sections, which the skilled person will know how to combine into a genetically modified cell capable of producing one or more sialylated HMO's.

The method particularly comprises culturing a genetically modified cell that produces a sialylated HMO, in particular the sialylated HMO 3'SL.

The method comprising culturing a genetically modified cell that produces a sialylated HMO and further comprises culturing said genetically engineered cell in in the presence of an energy source (carbon source) selected from the group consisting of glucose, sucrose, fructose, xylose and glycerol.

In one aspect, the method according to the present disclosure produces a sialylated human milk oligosaccharide (HMO), such as 3'SL, FSL, DSLNT and/or LST-a.

In one aspect, the method according to the present disclosure produces 3'SL as the only HMO.

To enable the production of sialylated HMOs in the method according to the present disclosure, the genetically modified cell may comprise a biosynthetic pathway for making a sialic acid sugar nucleotide, alternatively sialic acid can be added during cultivation of the cell.

In preferred embodiments of the methods of the present disclosure, the genetically modified cell comprises a biosynthetic pathway for making a sialic acid sugar nucleotide. Preferably, in methods of the present disclosure, the sialic acid sugar nucleotide is CMP-Neu5Ac. Thus, in methods of the present disclosure the sugar nucleotide pathway is expressed by the genetically modified cell, wherein the CMP-Neu5Ac pathway is encoded by the neuBCA operon from *Campylobacter jejuni* of SEQ ID NO: 35 In methods of the present disclosure, the sialic acid sugar nucleotide pathway is encoded from a high-copy plasmid bearing the neuBCA operon.

The method of the present disclosure comprises providing a glycosyl donor, which is synthesized separately by one or more genetically engineered cells and/or is exogenously added to the culture medium from an alternative source.

In one aspect, the method of the present disclosure further comprises providing an acceptor saccharide as substrate for the HMO formation, the acceptor saccharide comprising at least two monosaccharide units, which is exogenously added to the culture medium and/or has been produced by a separate microbial fermentation.

In one aspect, the method of the present disclosure comprises providing an acceptor saccharide comprising at least two monosaccharide units, which is exogenously added to the culture medium and/or has been produced by a separate microbial fermentation and which is selected form lactose, LNT-II and LNT, preferably lactose. In a preferred embodiment the substrate for HMO formation is lactose which is fed to the culture during the fermentation of the genetically engineered cell.

The sialylated human milk oligosaccharide (HMO) is retrieved from the culture, either from the culture medium and/or the genetically modified cell.

In particular, the present disclosure relates to a method for producing a sialylated HMO, said method comprising:

a) obtaining a genetically modified cell comprising
   i. a recombinant nucleic acid sequence, preferably under control of a PglpF promoter, encoding an enzyme with α-2,3-sialyltransferase activity, wherein said enzyme is selected from the group consisting of: Clari1 comprising or consisting of the amino acid sequence of SEQ ID NO: 1 or an amino acid sequence with at least 80%, such as at least 85%, such as at least 90%, such as at least 95%, or such as at least 99% identity to SEQ ID NO: 1, Neigon comprising or consisting of the amino acid sequence of SEQ ID NO: 2 or an amino acid sequence with at least 80%, such as at least 85%, such as at least 90%, such as at least 95%, or such as at least 99% identity to SEQ ID NO: 2, Poral comprising or consisting of the amino acid sequence of SEQ ID NO: 3 or an amino acid sequence with at least 80%, such as at least 80%, such as at least 90%, such as at least 95%, or such as at least 99% identity to SEQ ID NO: 3 and PmN comprising or consisting of the amino acid sequence of SEQ ID NO: 4 or an amino acid sequence with at least 80%, such as at least 85%, such as at least 90%, such as at least 95%, or such as at least 99% identity to SEQ ID NO: 4;
   ii. optionally a nucleic acid sequence encoding a heterologous β-1,3-galactosyltransferase, such as GalTK from *Helicobacter pylori*, preferably under control of a PglpF promoter,
   iii. optionally, a nuclei acid sequence encoding a β-1, 3-N-acetyl-glucosaminyl-transferase, such as LgtA from *Neisseria meningitidis*, preferably under control of a PglpF promoter and
   iv. optionally a nucleic acid sequence encoding an MFS transporter, such as but not limited to Fred, Nec and/or YberC, preferably under control of a PglpF or Plac promoter, and b) culturing said genetically modified cell in a carbon-source containing culture medium and in the presence of lactose, and c) producing said sialylated human milk oligosaccharide (HMO), in particular 3'SL and/or LST-a, by said genetically modified cell, and d) retrieving the sialylated human milk oligosaccharide (HMO), in particular 3'SL and/or LST-a, from the culture medium and/or the genetically modified cell.

In particular, the present disclosure relates to a method for producing 3'SL, said method comprising:
a) obtaining a genetically modified cell comprising
   i. a recombinant nucleic acid sequence encoding an enzyme with α-2,3-sialyltransferase activity, wherein said enzyme is Clari1 comprising or consisting of the amino acid sequence of SEQ ID NO: 1 or an amino acid sequence with at least 80%, such as at least 8%, such as at least 90%, such as at least 95%, or such as at least 99% identity to SEQ ID NO: 1 and
   ii. a nucleic acid sequence encoding an MFS transporter, such as but not limited to Fred, Nec and/or YberC, preferably under control of a PglpF or Plac promoter, and
b) culturing said genetically modified cell in a carbon-source containing culture medium and in the presence of lactose, and
c) producing said sialylated human milk oligosaccharide (HMO), in particular 3'SL, by said genetically modified cell, and
d) retrieving the sialylated human milk oligosaccharide (HMO), in particular 3'SL, from the culture medium and/or the genetically modified cell.

In particular, the present disclosure relates to a method for producing 3'SL, said method comprising:
a) obtaining a genetically modified cell comprising
   i. a recombinant nucleic acid sequence encoding an enzyme with α-2,3-sialyltransferase activity, wherein said enzyme is Poral comprising or consisting of the amino acid sequence of SEQ ID NO: 2 or an amino acid sequence with at least 80%, such as at least 85%, such as at least 90%, such as at least 95%, or such as at least 99% identity to SEQ ID NO: 2 and
   ii. a nucleic acid sequence encoding an MFS transporter, such as but not limited to Fred, Nec and/or YberC, preferably under control of a PglpF or Plac promoter, and
b) culturing said genetically modified cell in a carbon-source containing culture medium and in the presence of lactose, and
c) producing 3'SL, by said genetically modified cell, and
d) retrieving 3'SL, from the culture medium and/or the genetically modified cell.

In particular, the present disclosure relates to a method for producing 3'SL, said method comprising:
a) obtaining a genetically modified cell comprising
   i. a recombinant nucleic acid sequence encoding an enzyme with α-2,3-sialyltransferase activity, wherein said enzyme is Poral comprising or consisting of the amino acid sequence of SEQ ID NO: 3 or an amino acid sequence with at least 80%, such as at least 85%, such as at least 90%, such as at least 95%, or such as at least 99% identity to SEQ ID NO: 3 and
   ii. a nucleic acid sequence encoding an MFS transporter, such as but not limited to Fred, Nec and/or YberC, preferably under control of a PglpF or Plac promoter, and
b) culturing said genetically modified cell in a carbon-source containing culture medium and in the presence of lactose, and
c) producing 3'SL, by said genetically modified cell, and
d) retrieving the 3'SL, from the culture medium and/or the genetically modified cell.

In particular, the present disclosure relates to a method for producing 3'SL, said method comprising:
a) obtaining a genetically modified cell comprising
   i. a recombinant nucleic acid sequence encoding an enzyme with α-2,3-sialyltransferase activity, wherein said enzyme is PmN comprising or consisting of the amino acid sequence of SEQ ID NO: 4 or an amino acid sequence with at least 80%, such as at least 85%, such as at least 90%, such as at least 95%, or such as at least 99% identity to SEQ ID NO: 4 and
   ii. a nucleic acid sequence encoding an MFS transporter, such as but not limited to Fred, Nec and/or YberC, preferably under control of a PglpF or Plac promoter, and
b) culturing said genetically modified cell in a carbon-source containing culture medium and in the presence of lactose, and
c) producing 3'SL, by said genetically modified cell, and
d) retrieving 3'SL, from the culture medium and/or the genetically modified cell.

Culturing or fermenting (used interchangeably herein) in a controlled bioreactor typically comprises (a) a first phase of exponential cell growth in a culture medium ensured by a carbon-source, and (b) a second phase of cell growth in a culture medium run under carbon limitation, where the carbon-source is added continuously together with the acceptor oligosaccharide, such as lactose, allowing formation of the HMO product in this phase. By carbon (sugar) limitation is meant the stage in the fermentation where the growth rate is kinetically controlled by the concentration of the carbon source (sugar) in the culture broth, which in turn is determined by the rate of carbon addition (sugar feed-rate) to the fermenter.

The stability of a microbial strain when taken into large-scale production is important to obtain successful fermentation with high yield and product formation. Many factors during large-scale fermentation can cause the cells to become stressed and potentially reduce the metabolic activity or induce a change in metabolism to form toxic by-products such as acetic and formic acid, which leads to premature fermentation stop. Imperfect mixing during a large-scale fermentation creates gradients of for example gasses and carbon source, which the cells must be able to withstand. Unbalanced expression of heterologous genes introduced into the cell to produce the desired product, can induce toxicity that can reduce the maximum growth rate of the cells which in turn can trigger by-product formation, especially when exposed to carbon source gradients. In relation to the overexpression of the Nst α-2,3-sialyltransferase of SEQ ID NO: 5 to produce 3'SL in a genetically modified cell (Nst strain), the inventors have observed that the strain is less stable if the growth rate during the carbon limited stage becomes too high. It is desirable to have a strain that exhibits stable growth over a wider range of growth rates and also when exposed to gradients. Compared to the Nst strain, a strain expressing an α-2,3-sialyltransferase of the present disclosure is more flexible and capable of coping with more aggressive feeding profiles where a higher specific feed rates of the carbon source is used to yield higher volumetric productivities. Moreover, the cells are also better able to withstand pulsed versions of the sugar feeding profile that mimic the sugar gradients of large-scale fermentations. The stability of the genetically modified cells of the present disclosure can be compared to the stability of the Nst strain using the "growth stability test" and "stress test" described in the Method section.

The terms "manufacturing" or "manufacturing scale" or "large-scale production" or "large-scale fermentation", are used interchangeably and in the meaning of the disclosure defines a fermentation with a minimum volume of 100 L, such as 1000 L, such as 10.000 L, such as 100.000 L, such as 200.000 L culture broth. Usually, a "manufacturing scale" process is defined by being capable of processing large volumes yielding amounts of the HMO product of interest that meet, e.g., in the case of a therapeutic compound or composition, the demands for toxicity tests, clinical trials as well as for market supply. In addition to the large volume, a manufacturing scale method, as opposed to simple lab scale methods like shake flask cultivation, is characterized by the use of the technical system of a bioreactor (fermenter) which is equipped with devices for agitation, aeration, nutrient feeding, monitoring, and control of process parameters (pH, temperature, dissolved oxygen tension, back pressure, etc.). To a large extent, the behavior of an expression system in a lab scale method, such as shake flasks, benchtop bioreactors or the deep well format described in the examples of the disclosure, does allow to predict the behavior of that system in the complex environment of a bioreactor.

With regards to the suitable cell medium used in the fermentation process, there are no limitations. The culture medium may be semi-defined, i.e., containing complex media compounds (e.g., yeast extract, soy peptone, casamino acids, etc.), or it may be chemically defined, without any complex compounds. The carbon-source can be selected from the group consisting of glucose, sucrose, fructose, xylose, and glycerol. In one or more exemplary embodiments, the culturing media is supplemented with one or more energy and carbon sources selected form the group containing glycerol, sucrose, and glucose.

In one or more exemplary embodiments, the culturing media contains sucrose as the sole carbon and energy source. In one or more exemplary embodiments, the genetically engineered cell comprises one or more heterologous nucleic acid sequence encoding one or more heterologous polypeptide(s) which enables utilization of sucrose as sole carbon and energy source of said genetically engineered cell.

In one or more exemplary embodiments, the genetically engineered cell comprises a PTS-dependent sucrose utilization system, further comprising the scrYA and scrBR operons as described in WO2015/197082 (hereby incorporated by reference).

After carrying out the method of this disclosure, the sialylated HMO produced can be collected from the cell culture or fermentation broth in a conventional manner.

Retrieving/Harvesting

The sialylated human milk oligosaccharide (HMO) is retrieved from the culture medium and/or the genetically modified cell. In the present context, the term "retrieving" is used interchangeably with the term "harvesting". Both "retrieving" and "harvesting" in the context relate to collecting the produced HMO(s) from the culture/broth following the termination of fermentation. In one or more exemplary embodiments it may include collecting the HMO(s) included in both the biomass (i.e., the host cells) and cultivation media, i.e., before/without separation of the fermentation broth from the biomass. In other embodiments, the produced HMOs may be collected separately from the biomass and fermentation broth, i.e., after/following the separation of biomass from cultivation media (i.e., fermentation broth).

The separation of cells from the medium can be carried out with any of the methods well known to the skilled person in the art, such as any suitable type of centrifugation or filtration. The separation of cells from the medium can follow immediately after harvesting the fermentation broth or be carried out at a later stage after storing the fermentation broth at appropriate conditions. Recovery of the produced HMO(s) from the remaining biomass (or total fermentation broth) include extraction thereof from the biomass (i.e., the production cells).

After recovery from fermentation, HMO(s) are available for further processing and purification.

The HMOs can be purified according to the procedures known in the art, e.g., such as described in WO2017/182965 or WO2017/152918, wherein the latter describes purification of sialylated HMOs. The purified HMOs can be used as nutraceuticals, pharmaceuticals, or for any other purpose, e.g., for research.

At the end of culturing, the oligosaccharide as product can be accumulated both in the intra- and the extracellular matrix.

The method according to the present disclosure comprises cultivating the genetically engineered microbial cell in a culture medium which is designed to support the growth of microorganisms, and which contains one or more carbohydrate sources or just carbon-source, such as selected from the group consisting of glucose, sucrose, fructose, xylose and glycerol. In one or more exemplary embodiments, the culturing media is supplemented with one or more energy and carbon sources selected form the group containing glycerol, sucrose and glucose.

Manufactured Product

The term "manufactured product" according to the use of the genetically engineered cell or the nucleic acid construct refer to the one or more HMOs intended as the one or more product HMO(s). The various products are described above.

Advantageously, the methods disclosed herein provide both a decreased ratio of by-product to product and an increased overall yield of the product (and/or HMOs in total). This, less by-product formation in relation to product formation, facilitates an elevated product production and increases efficiency of both the production and product recovery process, providing superior manufacturing procedure of HMOs.

The manufactured product may be a powder, a composition, a suspension, or a gel comprising one or more HMOs.

Sequences

The current application contains a sequence listing in text format and electronical format which is hereby incorporated by reference.

An overview of the SEQ ID NOs used in the present application can be found in table 1 (alpha-2,3-sialyltransferase protein sequences), table 2 (promoter sequences) and table 4 (alpha-2,3-sialyltransferase DNA sequences), additional sequences described in the application is the DNA sequence encoding the neuBCA operon from *Campylobacter jejuni* (SEQ ID NO: 35), the β-1,3-N-acetylglucosaminyltransferase LgtA from *N. meningitidis* (SEQ ID NO: 36), β-1,3-galactosyltransferases galTK from *H. pylori* (SEQ ID NO: 37) and the MFS transporter sequences Nec (SEQ ID NO: 38), YberC (SEQ ID NO: 39) and Fred (SEQ ID NO: 40).

Embodiments

Various embodiments of present disclosure are described in the following clauses:

1. A genetically modified cell comprising a recombinant nucleic acid sequence encoding an enzyme with α-2,3- sialyltransferase activity, wherein said enzyme is selected from the group of sialyltransferases consisting of:
  a. Poral comprising or consisting of the amino acid sequence of SEQ ID NO: 3 or an amino acid sequence with at least 80%, such as at least 85%, such as at least 90%, such as at least 95% identity to SEQ ID NO: 3
  b. Clari1 comprising or consisting of the amino acid sequence of SEQ ID NO: 1 or an amino acid sequence with at least 80%, such as at least 85%, such as at least 90%, such as at least 95% identity to SEQ ID NO: 1,
  c. PmN comprising or consisting of the amino acid sequence of SEQ ID NO: 4 or an amino acid sequence with at least 80%, such as at least 85%, such as at least 90%, such as at least 95% identity to SEQ ID NO: 4, and
  d. Neigon comprising or consisting of the amino acid sequence of SEQ ID NO: 2 or an amino acid sequence with at least 80%, such as at least 85%, such as at least 90%, such as at least 95% identity to SEQ ID NO: 2, wherein said cell produces a sialylated HMO.

2. The genetically modified cell according to clause 1, wherein the sialylated HMO is selected from the group consisting of 3'SL, FSL, DSLNT and LST-a.

3. The genetically modified cell according to any of clauses 1 or 2, wherein the sialylated HMO is 3'SL.

4. The genetically modified cell according to any one of the preceding clauses, wherein 3'SL is the only HMO produced by the genetically modified cell.

5. The genetically modified cell according to any one of the preceding clauses, wherein the nucleic acid sequence encoding an enzyme with α-2,3-sialyltransferase activity is under the control of a promoter selected from the group consisting of PglpF, PglpA_70 UTR, PglpT_70 UTR, Plac_70 UTR, Pmg16_70 UTR and variants thereof, with a nucleic acid sequence according to SEQ ID NOs 12-22 or 41-54, preferably selected from the group consisting of SEQ ID NOs 13, 18, 19, 20, 21, 22, 41, 42, 43, 44, 45, 46, 47, 48, 49, 50 and 51.

6. The genetically modified cell according to any one of the preceding clauses, wherein the cell further comprises one or more nucleic acid sequences encoding one or more glycosyltransferases selected from the group consisting of β-1,3-galactosyltransferases, β-1,4-galactosyltransferases and β-1,3-N-acetyl-glucosaminyl-transferases.

7. The genetically modified cell according to any one of the preceding clauses, wherein the cell further comprises a nucleic acid sequence encoding an MFS transporter protein capable of exporting the sialylated HMO into the extracellular medium.

8. The genetically modified cell according to clause 7, wherein the MFS transporter protein is the Fred, YberC or Nec protein.

9. The genetically modified cell according to any one of the preceding clauses, wherein the cell comprises a biosynthetic pathway for making a sialic acid sugar nucleotide.

10. The genetically modified cell according to clause 9, wherein the sialic acid sugar nucleotide is CMP-Neu5Ac and said sialic acid sugar nucleotide pathway is encoded by the nucleic acid sequence encoding NeuBCA from *Campylobacter jejuni* (SEQ ID NO: 35).

11. The genetically modified cell according to clause 9 or 10, wherein the sialic acid sugar nucleotide pathway is encoded from a high-copy plasmid bearing the neuBCA operon.

12. The genetically modified cell according to any of the preceding clauses, wherein said modified cell is a microorganism.

13. The genetically modified cell according to any of the preceding clauses, wherein said modified cell is a bacterium or a fungus.

14. The genetically modified cell according to clause 13, wherein said fungus is selected from a yeast cell of the genera Komagataella, *Kluyveromyces, Yarrowia, Pichia, Saccharomyces, Schizosaccharomyces* or *Hansenula* or from a filamentous fungous of the genera *Aspargillus, Fusarium* or *Thricoderma*.

15. The genetically modified cell according to clause 13, wherein said bacterium is selected from the group consisting of *Escherichia* sp., *Bacillus* sp., *lactobacillus* sp. and *Campylobacter* sp.

16. The genetically modified cell according to clause 15 wherein said bacterium is *E. coli*.

17. A method for producing a sialylated human milk oligosaccharide (HMO), said method comprising culturing a genetically modified cell comprising a recombinant nucleic acid sequence encoding an enzyme with α-2,3-sialyltransferase activity, wherein said enzyme is selected from the group consisting of:
  a. Poral comprising or consisting of the amino acid sequence of SEQ ID NO: 3 or an amino acid sequence with at least 80%, such as at least 85%, such as at least 90%, such as at least 95% identity to SEQ ID NO: 3,
  b. Clari1 comprising or consisting of the amino acid sequence of SEQ ID NO: 1 or an amino acid sequence with at least 80%, such as at least 85%, such as at least 90%, such as at least 95% identity to SEQ ID NO: 1,
  c. PmN comprising or consisting of the amino acid sequence of SEQ ID NO: 4 or an amino acid sequence with at least 80%, such as at least 85%, such as at least 90%, such as at least 95% identity to SEQ ID NO: 4, and
  d. Neigon comprising or consisting of the amino acid sequence of SEQ ID NO: 2 or an amino acid sequence with at least 80%, such as at least 85%, such as at least 90%, such as at least 95% identity to SEQ ID NO: 2, wherein said genetically modified cell optionally comprises at least one additional modification according to clauses 4 to 11.

18. The method according to clause 17, wherein the sialylated human milk oligosaccharide (HMO) produced is 3'SL.

19. The method according to clause 17 or 18, wherein 3'SL is the only human milk oligosaccharide (HMO) produced.

20. The method according to any one of clauses 17 to 19, wherein the method comprises cultivating the genetically engineered cell in the presence of a carbon source selected from the group consisting of glucose, sucrose, fructose, xylose and glycerol.

21. The method according to any one of clauses 17 to 20, wherein lactose is added during the cultivation of the genetically engineered cells as a substrate for the sialylated HMO formation.

22. The method according to any one of clauses 17 to 21, wherein the sialylated human milk oligosaccharide (HMO) is retrieved from the culture medium and/or the genetically modified cell.

23. A nucleic acid construct comprising recombinant nucleic acid sequence encoding an enzyme with α-2,3-sialyltransferase activity, wherein said recombinant nucleic acid sequence is selected from the group consisting of:
  a. Poral comprising or consisting of the nucleic acid sequence of SEQ ID NO: 25 or an amino acid sequence with at least 80%, such as at least 85%, such as at least 90%, such as at least 95% identity to SEQ ID NO: 25,
b. Clari1 comprising or consisting of the nucleic acid sequence of SEQ ID NO: 23 or an amino acid sequence with at least 80%, such as at least 85%, such as at least 90%, such as at least 95% identity to SEQ ID NO: 23,
c. PmN comprising or consisting of the nucleic acid sequence of SEQ ID NO: 26 or an amino acid sequence with at least 80%, such as at least 85%, such as at least 90%, such as at least 95% identity to SEQ ID NO: 26
d. Neigon comprising or consisting of the nucleic acid sequence of SEQ ID NO: 24 or an amino acid sequence with at least 80%, such as at least 85%, such as at least 90%, such as at least 95% identity to SEQ ID NO: 24, wherein the enzyme encoding sequence is under the control of a promoter sequence.

24. The nucleic acid construct according to clause 23, wherein the promoter sequence is selected from the group consisting of PglpF, PglpA_70 UTR, PglpT_70 UTR, Plac_70 UTR, Pmgl13_70 UTR and variants thereof, with the nucleic acid sequences according to SEQ ID NOs 12-22 or 41-54, preferably selected from the group consisting of SEQ ID NOs 13, 18, 19, 20, 21, 22, 41, 42, 43, 44, 45, 46, 47, 48, 49, 50 and 51.

25. Use of a nucleic acid construct comprising according to clause 23 or 24, in a host cell for producing a sialylated HMO.

26. Use of a genetically modified cell according to any one of clauses 1 to 16, in the production of a sialylated HMO.

EXAMPLES

Methods

Unless stated otherwise, standard techniques, vectors, control sequence elements, and other expression system elements known in the field of molecular biology are used for nucleic acid manipulation, transformation, and expression. Such standard techniques, vectors, and elements can be found, e.g., in: Ausubel et al. (eds.), Current Protocols in Molecular Biology (1995) (John Wiley & Sons); Sambrook, Fritsch, & Maniatis (eds.), Molecular Cloning (1989) (Cold Spring Harbor Laboratory Press, NY); Berger & Kimmel, Methods in Enzymology 152: Guide to Molecular Cloning Techniques (1987) (Academic Press); Bukhari et al. (eds.), DNA Insertion Elements, Plasmids and Episomes (1977) (Cold Spring Harbor Laboratory Press, NY); Miller, J. H. Experiments in molecular genetics (1972) (Cold spring Harbor Laboratory Press, NY)

The embodiments described below are selected to illustrate the disclosure and are not limiting the disclosure in any way.

Enzymes:

18 enzymes were collected following an in-silico selection approach that was based on protein BLAST searches using known α-2,3-sialyltransferases as queries and by exploiting information sources such as scientific articles or databases, e.g., the KEGG and CAZY databases.

TABLE 3

List of the enzymes tested in the framework of the present disclosure

| Enzyme Name | GenBank ID | Enzyme length | Origin |
| --- | --- | --- | --- |
| Poral2 | WP_101774701.1 | 20 aa N-terminal deletion | Pasteurella oralis |
| Ccol2 | EAH6554614.1 | full length | Campylobacter coli |
| Cjej1 | EBD1936710.1 | full length | Campylobacter jejuni |
| Chepa | WP_066776435.1 | full length | Campylobacter hepaticus |
| Csub1 | WP_039664428.1 | full length | Campylobacter subantarcticus |
| CstI | AAF13495.1 | 130 aa C-terminal deletion | Campylobacter jejuni |
| Clari1 | EGK8106227.1 | full length | Campylobacter lari |
| CstII | AAF31771.1 | 32 aa C-terminal deletion | Campylobacter jejuni |
| Ccol | WP_075498955.1 | full length | Campylobacter coli |
| MhnN | WP_176810284.1 | full length | Mannheimia (multispecies) |
| Pmult | WP_005753497.1 | 24 aa N-terminal deletion | Pasteurela multocida |
| PM70 | AAK03258.1 | 31aa C-terminal deletion | Pasteurella multocida subsp. multocida str. Pm70 |
| Neigon | AAW89748.1 | 18 aa N-terminal deletion | Neisseria gonorrhoeae FA 1090 |
| Poral | WP_101774487.1 | full length | Pasteurella oralis |
| Cinf1 | WP_011272254.1 | full length | Haemophilus influenzae |
| PmN | WP_005726268.1 | full length | Pasteurella (multispecies) |
| Avi | WP_115249238.1 | 18 aa N-terminal deletion | Avibacterium avium |
| Nst | AAC44541.1 | 29 aa N-terminal deletion | Neisseria meningitidis MC58 |

Strains

The strains (genetically engineered cells) constructed in the present application were based on Escherichia coli K-12 DH1 with the genotype: F⁻, k⁻, gyrA96, recA1, relA1, endA1, thi-1, hsdR17, supE44. Additional modifications were made to the E. coli K-12 DH1 strain to generate the MDO strain with the following modifications: lacZ: deletion of 1.5 kbp, lacA: deletion of 0.5 kbp, nanKETA: deletion of 3.3 kbp, melA: deletion of 0.9 kbp, wcaJ: deletion of 0.5 kbp, mdoH: deletion of 0.5 kbp, and insertion of Plac promoter upstream of the gmd gene.

Methods of inserting gene(s) of interest into the genome of E. coli are well known to the person skilled in the art. Insertion of genetic cassettes into the E. coli chromosome can be done using gene gorging (see e.g., Herring and Blattner 2004 J. Bacteriol. 186: 2673-81 and Warming et al 2005 Nucleic Acids Res. 33(4): e36) with specific selection marker genes and screening methods.

Codon optimized DNA sequences encoding individual α-2,3-sialyltransferases were genomically integrated into the MDO strain. Additionally, each strain was transformed with a high-copy plasmid bearing the neuBCA operon from *Campylobacter jejuni* (SEQ ID NO: 35) under the control of the Plac promoter. The neuBCA operon encodes all the enzymes required for the formation of an activated sialic acid sugar nucleotide (CMP-Neu5Ac). CMP-Neu5Ac acts as a donor for the intended glycosyltransferase reaction facilitated by the α-2,3-sialyltransferase under investigation, i.e., the transfer of sialic acid from the activated sugar CMP-Neu5Ac to the terminal galactose of lactose (acceptor) to form 3'SL.

The genotypes of the background strain (MDO), and the α-2,3-sialyltransferase-expressing strains capable of producing 3'SL as the only HMO are provided in Table 4.

TABLE 4

Genotypes of the strains, capable of producing 3'SL used in the present examples.

| Strain ref | Genotype | 2,3-ST cDNA SEQ ID NO |
|---|---|---|
| MDO | F- λ- ΔendA1 ΔrecA1 ΔrelA1 ΔgyrA96 Δthi-1 glnV44 hsdR17(rk-mK-) ΔlacZ wcaF::Plac ΔnanKETA ΔlacA ΔmelA ΔwcaJ ΔmdoH | |
| Clari1 | MDO Clari1_opt(PglpF), pBS-neuBCA(Plac)-amp | 23 |
| Neigon | MDO Neigon_opt(PglpF), pBS-neuBCA(Plac)-amp | 24 |
| Poral | MDO Poral_opt(PglpF), pBS-neuBCA(Plac)-amp | 25 |
| Nst_plac | MDO nst_opt(Plac), pBS-neuBCA(Plac)-amp | 26 |
| PmN | MDO PmN_opt(PglpF), pBS-neuBCA(Plac)-amp | 27 |
| PM70 | MDO PM70_opt(PglpF), pBS-neuBCA(Plac)-amp | 28 |
| Pmult | MDO Pmult_opt(PglpF), pBS-neuBCA(Plac)-amp | 29 |
| Avi | MDO Avi_opt(PglpF) | 30 |
| MhnN | MDO MhnN_opt(PglpF), pBS-neuBCA(Plac)-amp | 31 |
| Csub1 | MDO Csub1_opt(PglpF) pBS-neuBCA(Plac)-amp | 32 |
| Ccol | MDO Ccol_opt(PglpF), pBS-neuBCA(Plac)-amp | 33 |
| Cstl | MDO Cstl_opt(PglpF), pBS-neuBCA(Plac)-amp | 34 |
| Nst_PglpF | MDO nst_opt(PglpF), pBS-neuBCA(Plac)-amp | 26 |

*2,3-ST is an abbreviation of alpha-2,3-sialyltransferase, and the sequence is inserted into the genome of the host strain.

Deep Well Assay

The strains were screened in 96 deep well plates using a 4-day protocol. During the first 24 hours, precultures were grown to high densities and subsequently transferred to a medium that allowed induction of gene expression and product formation. More specifically, during day 1, fresh precultures were prepared using a basal minimal medium supplemented with magnesium sulphate, thiamine, and glucose. The precultures were incubated for 24 hours at 34° C. and 1000 rpm shaking and then further transferred to a new basal minimal medium (BMM, pH 7.5) to start the main culture. The new BMM was supplemented with magnesium sulphate, thiamine, a bolus of 20% glucose solution (50 ul per 100 mL) and a bolus of 20% lactose solution (5 ml per 100 ml). Moreover, 50% sucrose solution was provided as carbon source, accompanied by the addition of sucrose hydrolase (invertase), so that glucose was released at a rate suitable for C-limited growth. IPTG (50 mg/ml) was added to induce gene expression and ampicillin antibiotic (100 mg/ml). The main cultures were incubated for 72 hours at 28° C. and 1000 rpm shaking.

Growth Stability Test

The *E. coli* strains were cultivated in 250 mL fermenters (Ambr 250 Bioreactor system, Sartorius) starting with 100 mL of mineral culture medium consisting of 6.9 g/L glucose and a mineral medium comprised of $(NH_4)_2HPO_4$, $KH_2PO_4$, $MgSO_4 \times 7H_2O$, KOH, NaOH, trace element solution, antifoam, and thiamine. The dissolved oxygen level was kept at 20% by a cascade of first agitation and then airflow starting at 700 rpm (up to max 4500 rpm) and 1 VVM (up to max 3 VVM). The pH was kept at 6.8 by titration with 8.5% $NH_4OH$ solution. The cultivations were started with 2% (v/v) inoculums from pre-cultures grown in a similar glucose containing medium. After depletion of the glucose contained in the batch medium, a feed solution containing 49% (w/w) glucose, $MgSO_4 \times 7H_2O$, trace metals and antifoam was fed continuously using the feed profile shown in FIG. 2 starting at an initial feed rate of 0.192 g glucose/h. The temperature was initially at 33° C. but was dropped to 28° C. with a 5 h ramp after 26 hours of feed (fig x). The growth and metabolic activity and state of the cells were followed by on-line measurements of reflectance and CO 2 evolution rate.

Example 1—In Vivo 3'SL Synthesis

Genetically modified cells expressing individual alpha-2, 3-sialyltransferase enzymes were screened for their ability to produce the sialylated HMO, 3'SL, as the only HMO when using lactose as the initial substrate.

A group of 18 enzymes (table 3) were compiled for testing their ability to synthesize 3'SL when introduced into a genetically modified cells producing activated sialic acid (CMP-Neu5Ac) and where the cell was feed with lactose as substrate for the HMO production.

Genetically modified strains expressing the 18 individual α-2,3-sialyltransferases (table 3) were generated as described in the "Method" section. The cells were screened in a in a fed-batch deep well assay setup as described in the "Method" section. The molar content of individual HMOs produced by the strains was measured by HPLC.

Table 4 lists the genotype of the 13 strains that produced 3'SL as the only HMO.

Nst is a well-known enzyme for the production of 3'SL and was used as positive control in the present example. Two strains with Nst expressed under control of either the PglpF or Plac promoter were generated, where the strain expressing Nst under control of the Plac promoter have a better growth compared to the strain expressing Nst under control of the PglpF promoter (10-fold stronger than Plac) as indicated by the optical density of the cells by the end of incubation (table 5). For this reason, Nst_Plac was used as reference.

The results of the 3'SL producing cells are shown in table 5 as the amount (molar content, mM) of 3'SL compared to the Nst_Plac strain (in percentage, %). 3'SL was the only HMO produced by the strain.

TABLE 5

3'SL molar content (mM) produced by each strain relative to 3'SL molar content (mM) produced by the Nst_Plac strain, and the optical density observed at the end of incubation.

| Strain ref. | 3'SL relative % | Optical density |
| --- | --- | --- |
| MDO | 0.0 | 5.1 |
| Clari1 | 115.5 | 4.1 |
| Neigon | 113.3 | 4.3 |
| Poral | 105.0 | 4.4 |
| Nst_Plac | 100.0 | 4.3 |
| PmN | 98.9 | 4.6 |
| PM70 | 95.6 | 4.2 |
| Pmult | 94.2 | 4.8 |
| Avi | 93.1 | 4.5 |
| MhnN | 68.8 | 4.7 |
| Csub1 | 53.5 | 3.7 |
| Ccol | 36.6 | 5.0 |
| Cstl | 31.2 | 3.9 |
| Nst_PglpF | 105.8 | 3.7 |

From the data presented in table 5 it can be seen that there are 3 enzymes (Clari1, Neigon and Poral) that can form 3'SL at a level that is at least 5% above the level of 3'SL formed by the Nst_Plac strain, while the enzyme PmN produced similar 3'SL levels as the Nst_Plac strain. These levels are also above the amount of 3'SL produced by Cstl and PM70 which are known in the prior art to form 3'SL. The relative amount of 3'SL produced by these strains is shown in FIG. 1.

In a deep well assay setup, bacterial cells can produce acids due to suboptimal oxygenation, especially towards the end of the experiments, where cultures have reached higher optical densities. Although the extent to which these acids are formed can affect final optical densities, the optical density at the end of incubation could be used as a proxy of how well the cells cope with expressing the heterologous α-2,3-sialyltransferase, the higher the density the better the growth. Based on this it can be seen that PmN has a more optimal growth than the Nst_Plac strain, indicating the strain tolerate the PmN α-2,3-sialyltransferase better than the Nst α-2,3-sialyltransferase, this is further supported by the significantly reduced growth of the Nst_PglpF strain where Nst is under the control of a stronger promoter and therefore is expressed at higher levels.

The α-2,3-sialyltransferase Clari1, Neigon, Poral and PmN expression is well tolerated by the strain when controlled by the strong promoter PglpF and produce more or equivalent amount of 3'SL when compared to the Nst_Plac strain which has similar growth properties.

Example 2— Growth Stability of α-2,3-Sialyltransferase Expressing Strains

The robustness of the strains expressing the α-2,3-sialyltransferases is important when upscaling the manufacture of 3'SL. In the present example the growth of the best performing strains from example 1, the strains expressing Clari1 or Poral, were compared to the strains expressing Nst under control of either the PglpF or Plac promoter.

The strains were fermented according to the Growth stability test described in the "Materials" section.

Figure 2:
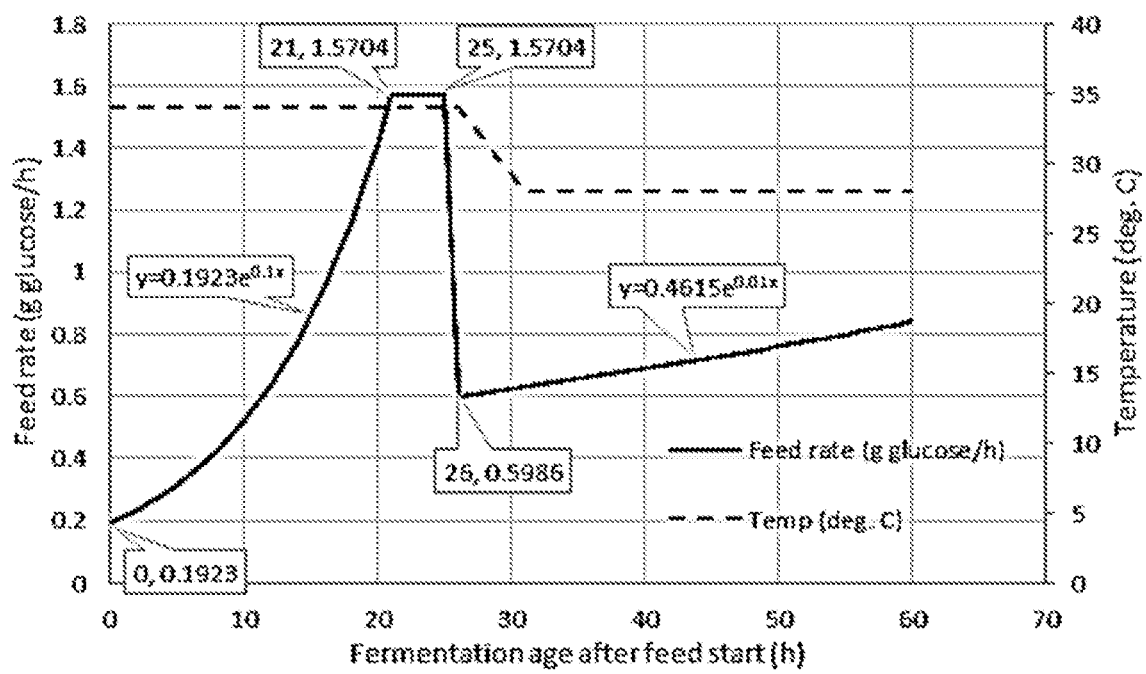
FIG. 2: Feed (solid line) and temperature (dotted line) profiles used in growth stability test.
Figure 3A:
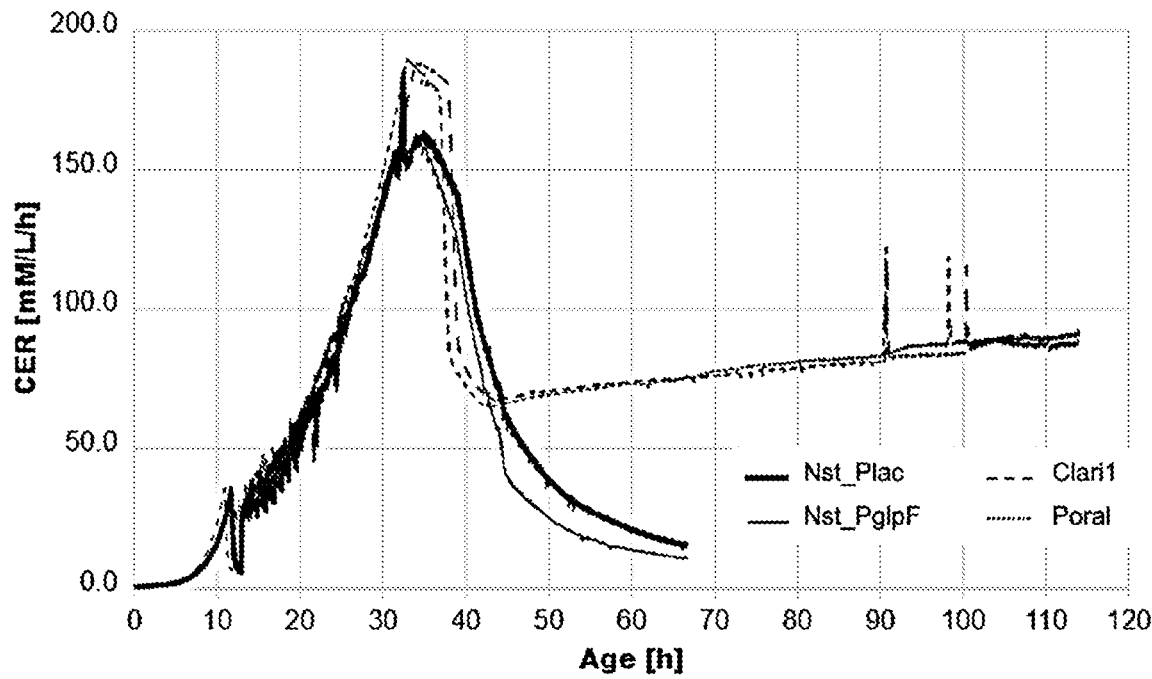
FIGS. 3A and 3B: Data from growth stability test of four different strains with Nst_Plac (bold line, Nst_PglpF (thin line), clari1 (dashed line) or poral (dotted line).

The carbon dioxide evolution rate (CER) recorded during the fermentation reflects the rate at which the cells produce $CO_2$ during the fermentation and essentially is a measure of the metabolism of the strain. If the CER drops it is an indication that the metabolism of the cells changes. In the growth stability test the feeding starts with a high glucose feeding rate which is then reduced significantly around 25 hours (FIG. 2). FIG. 3A shows the CER measured during the fermentation and shows that all strains have a drop in CER following the change in the feeding profile shown in FIG. 2. The strains with the α-2,3-sialyltransferase of the present disclosure, Clari1 (dashed line) and Poral (dotted line) both recover after the initial drop in CER at 35 hours, whereas the both the Nst strains with the Plac promoter (bold line) and the PglpF promoter (thin full line) never recover.

Figure 3B:
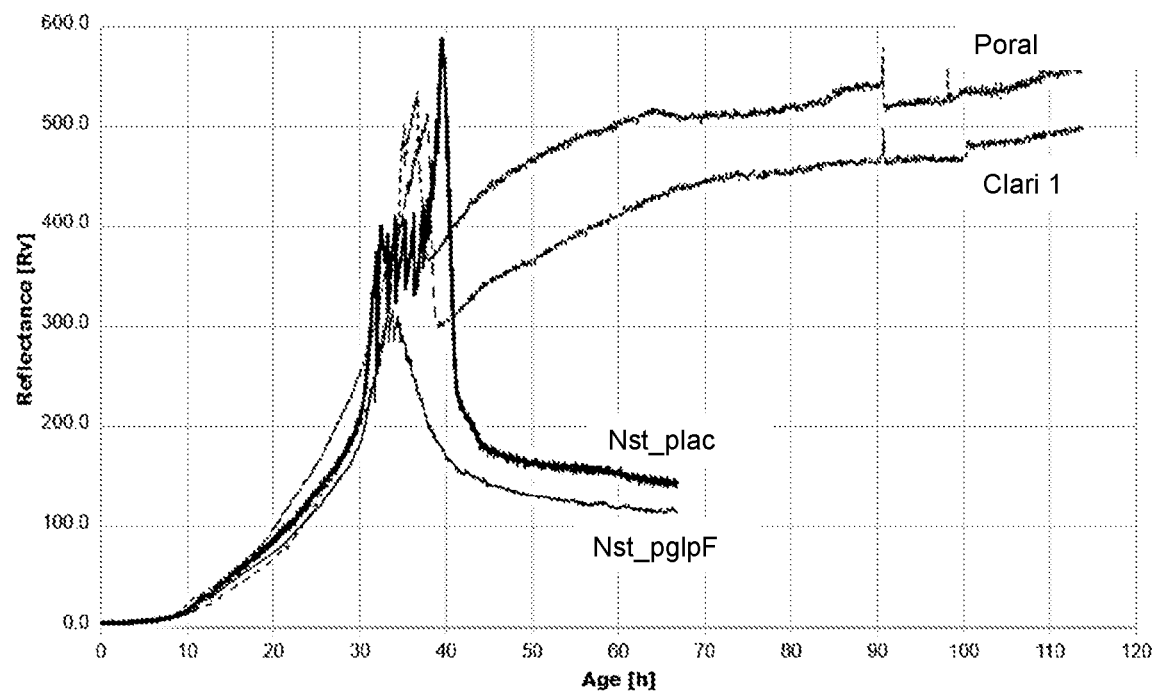

Reflectance measured during the fermentation in the Ambr 250 Bioreactor system is an indirect measure of the biomass in the reactor, which normally continues to increase throughout the fermentation. FIG. 3B shows the reflectance of the same fermentation as shown in FIG. 3A and also here it is clear that the strains expressing the α-2,3-sialyltransferase Poral and Clari1 maintain the ability to grow after the shift in the feeding profile, whereas the two Nst strains stop growing.

The invention claimed is:

1. A genetically modified cell comprising a heterologous recombinant nucleic acid sequence encoding an enzyme with α-2,3-sialyltransferase activity, wherein the enzyme is Poral with at least 80% identity to the amino acid sequence set forth in SEQ ID NO: 3, and wherein said cell produces a sialylated human milk oligosaccharide (HMO).

2. The genetically modified cell of claim 1, wherein the enzyme is Poral and comprises the amino acid sequence of SEQ ID NO: 3.

3. The genetically modified cell of claim 2, wherein the enzyme is Poral and consists of the amino acid sequence of SEQ ID NO: 3.

4. The genetically modified cell of claim 2, wherein the sialylated HMO is selected from the group consisting of 3'-sialyllactose (3'SL), 3-fucosyl-3'-sialyllactose (FSL), disialyl-lacto-N-tetraose (DSLNT) and 3'-O-sialyllacto-N-tetraose a (LST-a).

5. The genetically modified cell of claim 4, wherein the sialylated HMO is 3'SL.

6. The genetically modified cell of claim 5, wherein 3'SL is the only HMO produced by the genetically modified cell.

7. The genetically modified cell of claim 2, wherein the nucleic acid sequence encoding an enzyme with α-2,3-sialyltransferase activity is under the control of a promoter selected from the group consisting of PglpF, PglpA_70UTR, PglpT_70UTR, Plac_70UTR, PmglB_70UTR and variants thereof, with a nucleic acid sequence set forth in SEQ ID NOs 12-22 or 41-54.

8. The genetically modified cell of claim 7, wherein the nucleic acid sequence is selected from the group consisting of SEQ ID NOs 13, 18, 19, 20, 21, 22, 41, 42, 43, 44, 45, 46, 47, 48, 49, 50 and 51.

9. The genetically modified cell of claim 2, wherein the cell further comprises a nucleic acid sequence encoding an major facilitator superfamily (MFS) transporter protein capable of exporting the sialylated HMO into the extracellular medium.

10. The genetically modified cell of claim 9, wherein the MFS transporter protein is the Fred protein comprising the amino acid sequence set forth in SEQ ID NO: 40, YberC protein comprising the amino acid sequence set forth in SEQ ID NO:39, or Nec protein comprising the amino acid sequence set forth in SEQ ID NO: 38.

11. The genetically modified cell of claim 2, wherein the cell comprises a biosynthetic pathway for making a sialic acid sugar nucleotide.

12. The genetically modified cell of claim 2, wherein the modified cell is a microorganism selected from group consisting of a bacterium and a fungus.

13. The genetically modified cell of claim 12, wherein the fungus is a yeast cell of the genera Komagataella, *Kluyveromyces, Yarrowia, Pichia, Saccaromyces, Schizosaccharomyces* or *Hansenula*, or from a filamentous fungous of the genera *Aspargillus, Fusarium*, or Thricoiderma; or the bacterium is selected from the group consisting of *Escherichia* sp., *Bacillus* sp., *Corynebacterium* sp., *lactobacillus* sp. and *Campylobacter* sp.

14. The genetically modified cell of claim 13, wherein said bacterium is *E. coli*.

15. A method for producing a sialylated human milk oligosaccharide (HMO) comprising: culturing a the genetically modified cell of claim 2.

16. The method of claim 15, wherein the genetically modified cell is the genetically modified cell of claim 10.

17. The method of claim 15, wherein the sialylated human milk oligosaccharide (HMO) produced is 3'SL.

18. The method of claim 17, wherein 3'SL is the only human milk oligosaccharide (HMO) produced.

19. The method of claim 15, further comprising adding lactose during the culturing step.

20. The method of claim 15, further comprising retrieving the sialylated human milk oligosaccharide (HMO) from the culture medium or the genetically modified cell.

* * * * *